United States Patent
Dannhardt et al.

(10) Patent No.: US 9,364,459 B2
(45) Date of Patent: Jun. 14, 2016

(54) 3-(INDOLYL)- OR 3-(AZAINDOLYL)-4-ARYLMALEIMIDE DERIVATIVES FOR USE IN THE TREATMENT OF COLON AND GASTRIC ADENOCARCINOMA

(75) Inventors: Gerd Dannhardt, Mainz (DE); Stanislav Plutizki, Mainz (DE); Jan-Peter Kramb, Mainz (DE); Annett Müller, Griesheim (DE); Markus Möhler, Mainz (DE)

(73) Assignees: Johannes Gutenberg-Universität Mainz, Mainz (DE); Universitätsmedizin der Johannes Gutenberg-Universität Mainz, Manz (DE)

( * ) Notice: Subject to any disclaimer, the term of this patent is extended or adjusted under 35 U.S.C. 154(b) by 0 days.

(21) Appl. No.: 13/516,992

(22) PCT Filed: Dec. 10, 2010

(86) PCT No.: PCT/EP2010/069349
§ 371 (c)(1),
(2), (4) Date: Oct. 8, 2012

(87) PCT Pub. No.: WO2011/073091
PCT Pub. Date: Jun. 23, 2011

(65) Prior Publication Data
US 2013/0029986 A1    Jan. 31, 2013

(30) Foreign Application Priority Data
Dec. 18, 2009  (EP) .................................. 09179984

(51) Int. Cl.
A61K 31/404    (2006.01)
A61K 31/5377   (2006.01)
A61K 31/4045   (2006.01)
A61P 35/00     (2006.01)
A61K 31/437    (2006.01)

(52) U.S. Cl.
CPC ............ *A61K 31/404* (2013.01); *A61K 31/437* (2013.01)

(58) Field of Classification Search
CPC ........... A61K 2300/00; A61K 31/404; A61K 31/437; A61K 31/454; A61K 31/4439; A61K 31/4412; A61K 31/40; A61K 31/7068; A61K 31/4025; A61K 31/4155
See application file for complete search history.

(56) References Cited

U.S. PATENT DOCUMENTS

| 8,008,320 | B2 | 8/2011 | Dannhardt |
| 8,841,319 | B2 | 9/2014 | Dannhardt |
| 2013/0131060 | A1 | 5/2013 | Dannhardt |
| 2013/0345281 | A1 | 12/2013 | Dannhardt |

FOREIGN PATENT DOCUMENTS

| EP | 1845094 A1 | 10/2007 |
| WO | WO 02/085459 A2 | 10/2002 |
| WO | WO 03/095452 A2 | 11/2003 |
| WO | WO 03/103663 A2 | 12/2003 |
| WO | WO 2004/094422 A1 | 11/2004 |
| WO | WO 2006/006939 A1 | 1/2006 |
| WO | WO 2006/061212 A1 | 6/2006 |
| WO | WO 2006/073202 A1 | 7/2006 |
| WO | WO 2009/071620 A1 | 6/2009 |
| WO | WO 2009/073869 A1 | 6/2009 |
| WO | WO 2011/073092 A1 | 6/2011 |

OTHER PUBLICATIONS

Fuchs et al ("Irinotecan in the treatment of colorectal cancer." Cancer Treatment Reviews, 2006; 32:491-503.).*
Of Iqbal et al ("Angiogenesis Inhibitors in the Treatment of Colorectal Cancer." Semin Oncol 2004; 31(suppl 17):10-16).*
Cohen et al ("FDA Drug Approval Summary: Bevacizumab Plus FOLFOX4 as Second-Line Treatment of Colorectal Cancer." The Oncologist 2007;12:356-361).*
Peifer et al ("Design, Synthesis, and Biological Evaluation of Novel 3-Aryl-4-(1H-indole-3yl)-1,5-dihydro-2H-pyrrole-2-ones as Vascular Endothelial Growth Factor Receptor (VEGF-R) Inhibitors." J Med Chem, 2008; 51(13):3814-3824).*
Weekes et al ("Irinotecan therapy and molecular targets in colorectal cancer: A systemic review." World J Gastroenterol, 2009; 15(29): 3597-3602).*
Berenbaum (Clin. Exp. Immunol., 1977; 28:1-18).*
Fuchs et al (Cancer Treatment Reviews, 2006; 32:491-503).*
Chou (Cancer Res, 2010; 70:440-446).*
Chung et al., "Adjuvant Therapy of Colon Cancer: Current Status and Future Directions", *The Cancer Journal*, vol. 13, No. 3, 192-197 (2007).
Koizumi et al., "Novel SN-38-Incorporating Polymeric Micelles, NK012, Eradicate Vascular Endothelial Growth Factor—Secreting Bulky Tumors", *Cancer Res.*, 66 (20), 10048-10056 (2006).
Ling et al., "The role of protein kinase C in the synergistic interaction of safingol and irinotecan in colon cancer cells", *International Journal of Oncology*, 35, 1463-1471 (2009).

(Continued)

*Primary Examiner* — Marcos Sznaidman
*Assistant Examiner* — Rayna B Rodriguez
(74) *Attorney, Agent, or Firm* — Viksnins Harris & Padys PLLP

(57) ABSTRACT

The present invention relates to the use of a compound of formula (I) wherein $R^1$ and $R^3$ are as defined in the description and $R^2$ is a phenyl group which is substituted with 2 or 3 $C_1$-$C_6$ alkoxy groups, or a physiologically acceptable salt thereof, or a solvate of the compound of formula (I) or of the salt thereof, for treatment of colorectal or gastric adenocarcinoma.

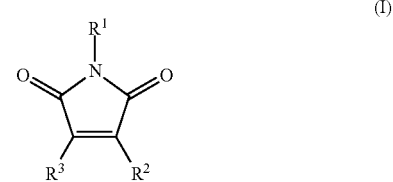

(I)

4 Claims, No Drawings

(56) References Cited

OTHER PUBLICATIONS

Patent Cooperation Treaty, International Searching Authority, Search Report and Written Opinion for PCT/EP2010/069349, 11 pages, Feb. 22, 2011.

Pommier, "Topoisomerase I inhibitors: camptothecins and beyond", *Nature Reviews, Cancer,* vol. 6, 789-802 (2006).

Shakoori et al., "Inhibition of GSK-3β activity attenuates proliferation of human colon cancer cells in rodents", *Cancer Sci.* vol. 98, No. 9, 1388-1393 (2007).

Zhang et al., "3-(7-Azaindolyl)-4-arylmaleimides as potent, selective inhibitors of glycogen synthase kinase-3", *Bioorganic & Medicinal Chemistry Letters,* 14, 3245-3250 (2004).

Varey et al., "VEGF 165b, an antiangiogenic VEGF-A isoform, binds and inhibits bevacizumab treatment in experimental colorectal carcinoma: balance of pro- and antiangiogenic VEGF-A isoforms has implications for therapy", *British Journal of Cancer* 98, 1366-1379 (2008).

* cited by examiner

3-(INDOLYL)- OR 3-(AZAINDOLYL)-4-ARYLMALEIMIDE DERIVATIVES FOR USE IN THE TREATMENT OF COLON AND GASTRIC ADENOCARCINOMA

RELATED APPLICATIONS

This application is a U.S. 371 application of PCT/EP2010/069349, which was filed on 10 Dec. 2010, and claims the benefit of priority of European Application Serial No. 09179984.1, which was filed on 18 Dec. 2009.

The present invention relates to the use of 3-(indolyl)- or 3-(azaindolyl)-4-arylmaleimide derivatives for treatment of colorectal or gastric adenocarcinoma.

Cancer is currently one of the most frequent causes of death in industrialized countries, and gastrointestinal carcinomas are among the most common types of cancer. There is, however, still no causal therapy available. Standard therapy of colorectal cancer basically consists of primary surgical resection and adjuvant cytotoxic chemotherapy involving agents such as 5-fluorouracil (5-FU), leucovorin, capecitabine, irinotecan, bevacizumab, cetuximab and oxiplatin. Radical surgery represents the standard form of curative gastric cancer therapy and is in general accompanied by treatment with chemotherapeutics such as 5-FU, leucovorin, epirubicin, docetaxel, cisplatin and sometimes also concurrent radiation therapy. As these methods can severely impair a patient's quality of life there is strong interest in advances in therapy: In particular attention is focused on achieving a high target cell selectivity of cancer treatment and on overcoming escape mechanisms such as the development of drug resistances which often occur by the accumulation of mutations in rapidly dividing cancer cells.

Protein kinases are an interesting class of target molecules for such improved therapeutic attempts. These proteins are known to regulate the majority of cellular pathways including such relevant for control cell growth, movement and death—all processes relevant for cancer growth and progression. In fact, the tyrosine kinases act primarily as growth factor receptors. Deregulation of protein kinases is a frequent cause of diseases, in particular cancer. Some protein kinase inhibitors including monoclonal antibodies such as trastuzumab, cetuximab, panitumumab, rituximab and bevacizumab as well as small molecules such as imatinib, gefitinib, erlotinib, sorafenib and sunitinib are therefore useful for treating cancer.

A physiological process often focused on in development of anti-cancer agents is apoptosis, a controlled form of cell death eliminating damaged, aberrant, infected, old or superfluous cells. In particular mucosa tissue such as gastrointestinal mucosa is characterized by a rapid epithelial cell turnover in which homeostasis is maintained predominantly by apoptosis. In the course of cancer development the capability of cells to undergo apoptosis is usually reduced, i.e. cancer cells are not or less susceptible to apoptotic signals. Agents that are able to promote readiness of apoptosis or induce apoptosis in cancer cells (pro-apoptotic agents) may therefore be useful for prevention and/or therapy of cancer, including colorectal or gastric adenocarcinoma. In fact, when treating cancer it is desirable to avoid violent destruction of cancer cells which will lead to "unclean" necrotic cell death including the release of cell contents and fragments into the extracellular environment, thus promoting inflammation and other undesirable side effects. It is therefore preferable to induce the less noxious programmed cell death (apoptosis). This physiological process leads to an orderly self-destruction without the release of toxins or pro-inflammatory substances into the surrounding tissue. The application of pro-apoptotic agents is therefore an attractive means to achieve a less injurious removal of cancer cells or to increase their sensitivity to conventional treatments, which would allow to reduce both dosage (and thus systemic side effects) and secondary effects caused by necrotic cell death.

One essential prerequisite for growth and metastasis of cancers which form tumors is angiogenesis, a process involving the formation of new blood vessels from pre-existing capillary endothelial cells. When reaching a certain size, generally about 3 mm$^3$, further growth of a cluster of cancer cells becomes completely dependent on angiogenesis which is required for supplying the cells with oxygen and other essential nutrients and probably also for removing their metabolic waste. Cells breaking away from an established tumor may enter the blood vessel and be carried to a distant site to start a secondary tumor there (metastasis). Tumor cells may enhance angiogenesis by overexpression of pro-angiogenic factors, e.g. VEGF, FGF2, PDGF and interleukins, but also by down-regulation of inhibitory factors, e.g. thrombospondin. In general, this is especially pronounced with tumors having a high microvessel density as well as a particular aggressive behavior and high tendency to metastasize. Therefore, inhibitors of angiogenesis are researched as antitumor agents.

Moguntinones, a class of small molecule compounds developed at the Johannes Gutenberg University Mainz comprise 3-(indolyl)- or 3-(azaindolyl)-4-arylmaleimide derivatives with tumor and vascular targeting properties.

WO 2006/061212 describes 3-(indolyl)- or 3-(azaindolyl)-4-arylmaleimide derivatives which are angiogenesis inhibitors and proposes their use for controlling angiogenesis and/or vascular dysfunction.

The use of certain 3-(indolyl)- or 3-(azaindolyl)-4-arylmaleimide derivatives showing an inhibitory effect on the protein kinase FTL3 for treatment and prevention of leukemia is described in WO 2009/071620.

It was an object of the present invention to provide a new use of 3-(indolyl)- or 3-(azaindolyl)-4-arylmaleimide derivatives.

Surprisingly, it has been found that certain 3-(indolyl)- or 3-(azaindolyl)-4-arylmaleimide derivatives selectively inhibit certain protein kinases and are not only effective angiogenetic inhibitors but also directly affect colon and stomach cancer cells by promoting or inducing apoptosis and/or decreasing the cell viability, and are thus useful for treatment of gastric and colorectal adenocarinomas.

The present invention relates to the use of a compound of formula (I):

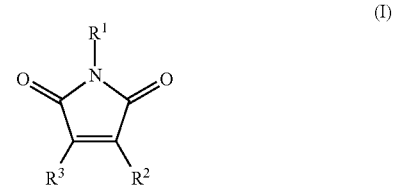

(I)

wherein
R$^1$ is H, C$_1$-C$_6$-alkyl, phenyl-C$_1$-C$_4$-alkyl or phenyl;
R$^2$ is a phenyl group which is substituted with 2 or 3 C$_1$-C$_6$-alkoxy groups, and
R$^3$ is indolyl or azaindolyl which may carry one, two or three substituents independently selected from C$_1$-C$_6$-alkyl, C$_1$-C$_6$-alkoxy, phenyl, OH, halogen, NH$_2$, C$_1$-C$_6$-alkylamino, di-C$_1$-C$_6$-alkylamino, C$_1$-C$_6$-alkyl-R$^{10}$, heteroaryl with 5 or 6 ring atoms containing 1 or 2 heteroatoms which are independently selected from O, N, and S, or heterocyclyl with 5 or 6 ring atoms containing 1 or 2 heteroatoms which are independently selected from O, N, and S, wherein $R^{10}$ is selected from:
a) amino,
b) $C_1$-$C_6$-alkylamino,
c) di-$C_1$-$C_6$-alkylamino,
d) hydroxy,
e) $C_1$-$C_6$-alkoxy,
f) saturated heterocyclyl with 5 or 6 ring atoms containing a nitrogen heteroatom and optionally 1 or 2 additional heteroatoms which are independently selected from O, N and S, wherein the heterocyclyl is attached to the $C_1$-$C_6$-alkyl group via the nitrogen atom and may carry one, two, three or four $C_1$-$C_6$-alkyl substituents;
g) phenoxy,
h) benzyloxy,
i) $R^{11}CONR^{12}$—,
j) $NR^{12}R^{12}CO$—,
k) $C_1$-$C_6$-alkyl-NHCONH—,
l) $C_1$-$C_6$-alkyl-NHCOO—,
m) $C_1$-$C_6$-alkyl-OCONH—,
n) $R^{12}$—$OSO_2O$—,
o) $R^{11}SO_2O$—,
p) $R^{12}$—$OSO_2$—,
q) $R^{11}SO_2$—,
r) $(R^{12}O)_2P(O)O$—,
s) $(R^{12}O)_2P(O)$—, and
t) $(R^{12}O)R_{11}P(O)O$—,
$R_{11}$ is $C_1$-$C_6$-alkyl and $R^{12}$ is $C_1$-$C_6$-alkyl;
a physiologically acceptable salt thereof, or a solvate of the compound of formula (I) or of the salt thereof in the treatment of colorectal or gastric adenocarcinoma.

Thus, the present invention is concerned with compounds of formula (I), physiologically acceptable salts or solvates thereof for use in treatment of colorectal or gastric adenocarcinoma. In particular, the present invention relates to the use of a compound of formula (I), a physiologically acceptable salt or solvate thereof as defined herein, in the manufacture of a medicament for treating colorectal or gastric adenocarcinoma.

The present invention also relates to a method of treating colorectal or gastric adenocarcinoma in a subject which comprises administering to said subject an amount, therapeutically effective for treating colorectal or gastric adenocarcinoma, of one or more compound(s) of formula (I), a physiologically acceptable salt or solvate thereof as defined herein.

Further, the present invention relates to the use of one or more compound(s) of formula (I) or a physiologically acceptable salt or solvate thereof as defined herein in the treatment of colorectal or gastric adenocarcinoma comprising the administration of a further chemotherapeutic agent.

The term "adenocarinoma" refers to a cancer which forms a tumor (i.e. a malignant tumor) originating in the epithelial cells of glandular tissue, e.g. gastric and colorectal mucosa, or in which the tumor cells form a recognizable glandular structure. A malignant tumor is a new growth of tissue in which cell multiplication is uncontrolled and progressive for this reason necrosis and ulceration are characteristic. Additionally, malignant tumors tend to invade surrounding tissue and are metastatic, initiating the growth of similar tumors in distant organs.

Gastric adenocarcinoma accounts for 95% of gastric cancer and like most malignancies has a multifactorial etiology. Nitrate derivatives, vitamin deficiencies, the consumption of alcohol and cigarettes, genetic predisposition and infection with *Helicobacter pylori* are discussed risk factors for gastric cancer development. Colorectal adenocarcinomas account for the large majority of colorectal cancers and show an increasing frequency in the Western world. Dietary factors, such as low fibre high fat and red meat, genetic predisposition and genetic diseases, e.g. ulcerative colitis or Crohn's disease, are suggested to increase the risk of developing colorectal cancer. Colon carcinomas mostly appear as a slowly growing, polypoid or annular mass of tissue; flat ulcerated lesions are rarely seen.

The term "treatment" as used herein means an intervention performed to prevent the development or to alter the pathology of a disorder and comprising the administration of one or more pharmaceutically active agents. Thus "treatment" refers to a therapeutic treatment as well as to a prophylactic or preventative treatment. A therapeutic treatment is performed with the aim of partial or total inhibition of cancer growth and partial or total destruction of the cancer cells, i.e. the cells constituting or resulting from the cancer. A preventative treatment aims to prevent the onset of clinically evident cancer altogether as well as to prevent the onset of a clinically evident stage in subjects at risk. It also encompasses the prevention of premalignant cells to malignant cells and includes a prophylactic treatment of subjects at risk of developing cancer.

As used herein, the term "subject" for purposes of treatment includes any mammalian, preferably human, subject who has or may have any form of gastric or colorectal adenocarcinoma or who is at risk for developing said cancer.

As used herein, the term "being at risk" refers to having a risk that is higher, preferably significantly higher, of developing gastric or colorectal adenocarcinoma than the majority of its reference group defined by basic medical factors such as age, gender, weight, etc., well-known to the skilled person. The subject may be at risk due to exposure to carcinogenic agents, e.g. ionizing radiation or chemical mutagens, genetic predisposition to develop said cancer, and the like.

According to a particular embodiment, the subject to be treated will not benefit from conventional therapy, e.g. surgery, irradiation or chemotherapy, in the absence of the administration of compounds of formula (I), physiologically acceptable salts or solvates thereof. The term "benefit" herein being used to denote the attainment of any or all of the objects of treatment as defined above.

In a particular embodiment, the invention relates to the treatment of refractory gastric or colorectal adenocarcinoma.

The term "refractory" as used herein refers to a cancer treated with currently available therapies such as surgery, chemotherapy and/or radiation therapy, wherein the therapy is not clinically adequate to treat the subject who, e.g., does not or only insufficiently respond to the treatment and thus needs additional effective therapy. Such cancer is also called resistant cancer, in particular referring to resistance of cancer cells to conventional chemotherapeutics, preferably the multidrug resistant (MDR) phenotype. Such resistance shows as a reduced efficiency of a chemotherapeutic agent, i.e. the dosage required to kill or arrest the cell division of the tissue which the cancer is derived from does affect resistant cells to a significantly less extent. The term "MDR" refers to a resistance to multiple different drugs achieved by mechanisms comprising increased drug efflux by proteins capable of clearing various types of chemotherapeutics, enzymatic drug deactivation, decreased cell permeability to a drug, altered drug binding sites and/or alternate metabolic pathways by which cancer cells may compensate for the effect of a drug. The term "refractory" can also describe subjects who respond to therapy yet suffer from side effects, relapse, develop resistance, etc. In various embodiments, "refractory" means that at least some significant portion of the cancer cells is not killed or their cell division not arrested (also referred to as minimal residual disease, MRD). The determination of whether a gastric or colorectal adenocarcinoma is "refractory" can be made either in vivo or in vitro by any method known in the art for assaying the effectiveness of treatment on cancer cells, using the art-accepted meanings of "refractory" in such a context.

In a particular embodiment, the invention relates to a treatment of gastric or colorectal cancer comprising the administration of one or more compounds of formula (I), physiologically acceptable salts or solvates thereof as well as further stimulation of cell death by a conventional method or a combination of conventional methods (combination therapy).

The conventional methods are preferably selected from the group consisting of surgery, irradiation, e.g. external irradiation or administration of radioactive compounds, and treatment with one or more chemotherapeutic agent(s) other than the compounds of the present invention including antineoplastic agents, multidrug resistance reversing agents, and biological response modifiers, and combinations thereof, examples being given below. Thus, the invention encompasses treatment regimens or protocols that provide better therapeutic profiles than current single agent therapies or current combination therapy regimens. Encompassed by the invention are combination therapies that have additive potency or an additive therapeutic effect as well as synergistic combinations where the therapeutic ratio is greater than additive.

The combination therapies encompassed by the invention provide an improved overall therapy relative to administration of either a compound of formula (I), a physiologically acceptable salt or solvate thereof or any conventional therapy alone. Preferably, such combinations also reduce or avoid unwanted or adverse effects. Thus, in certain embodiments, doses of existing or experimental cancer therapies can be reduced or administered less frequently which increases patient compliance, improves therapy and reduces unwanted or adverse effects.

Suitable antineoplastic agents may be selected from the group comprising compounds affecting integrity and synthesis of DNA, e.g. topoisomerase I inhibitors; alkylating agents: intercalating agents or DNA-binding antibiotics; antimitotic compounds such as taxanes: vinca alkaloids or colchicine derivatives; compounds for targeted cancer therapy such as protein kinase inhibitors, antibodies binding to cell membrane receptors and soluble decoy receptors; compounds affecting the cell metabolism, e.g. farnesyltransferase inhibitors, purin or pyrimidin analogues.

Examples for antineoplastic agents are aflibercept, asparaginase, bleomycin, busulfan, carmustine, chlorambucil, cladribine, cyclophosphamide, cytarabine, dacarbazine, daunorubicin, doxorubicin, etoposide, fludarabine, gemcitabine, hydroxyurea, idarubicin, ifosfamide, irinotecan, lomustine, mechlorethamine, melphalan, mercaptopurine, methotrexate, mitomycin, mitoxantrone, pentostatin, procarbazine, 6-thioguanine, topotecan, vinblastine, vincristine, retinoic acid, oxaliplatin, cis-platin, carboplatin, 5-FU (5-fluorouracil), teniposide, amasacrine, docetaxel, paclitaxel, vinorelbine, bortezomib, clofarabine, capecitabine, actinomycin D, epirubicine, vindesine, methotrexate, tioguanine (6-thioguanine) tipifarnib.

Examples for antineoplastic agents which are protein kinase inhibitors include imatinib, erlotinib, sorafenib, sunitinib, dasatinib, nilotinib, lapatinib, gefitinib, temsirolimus, everolimus, rapamycine, bosutinib, pzopanib, axitinib, neratinib, vatalanib, pazopanib, midostaurin and enzastaurin.

Examples for antineoplastic agents which are antibodies comprise trastuzumab, cetuximab, panitumumab, rituximab, bevacizumab, mapatumumab, conatumumab, lexatumumab and the like.

An example for a multidrug resistance reversing agent is PSC 833, a potent inhibitor of the efflux of antitumor drugs mediated by P-glycoprotein.

Suitable biological response modifiers may be selected from the group consisting of monoclonal antibodies and cytokines, such as interferons, interleukins and colony-stimulating factors, e.g., rituxan, CMA-676, interferon-alpha recombinant, interleukin-2, interleukin-3, erythropoetin, epoetin, G-CSF, GM-CSF, filgrastim, sargramostim and thrombopoietin.

According to a particular embodiment, the further chemotherapeutic agent is a topoisomerase I inhibitor and especially camptothecin or a derivative thereof such as described by Pommier, Y. (2006), Nature Reviews Cancer 6: 789-802. Examples for topomerase I inhibitors comprise compounds such as irinotecan (in particular irinotecan hydrochloride), topotecan (in particular topotecan hydrochloride), rubitecan, exatecan (in particular exatecan mesylate), lurtotecan, gimatecan, prothecan, karenitecin, belotecan (in particular belotecan hydrochloride), silatecan or diflomotecan and the salts thereof.

In a further embodiment, the compound of formula (I), a physiologically acceptable salt or derivative thereof shows a pro-apoptotic effect, i.e. promotes readiness of apoptosis or induces apoptosis of cancer cells of, e.g., gastric or colorectal adenocarcinoma in vitro or in vivo. Thus, the invention relates to a use of compounds of formula (I) for treatment of gastric or colorectal adenocarcinoma which involves said pro-apoptotic effects.

The term "induce apoptosis" is used herein to denote any significant increase in the rate of apoptosis in cells treated with compounds of formula (I), physiologically acceptable salts or derivatives thereof, compared to cells kept under otherwise identical conditions but not treated with said compounds, physiologically acceptable salts or derivatives thereof. The term "promote" is used herein to denote any significant increase in the rate of apoptosis in cells treated with compounds of formula (I), physiologically acceptable salts or derivatives thereof and one or more further agent(s) compared to cells kept under otherwise identical conditions including the further agent(s) but not the compounds of formula (I), physiologically acceptable salts or derivatives thereof. The term "stimulate" is used herein to denote any inducing or promoting effect.

It is particularly preferred if the use is for the restoration of the natural ability to undergo apoptosis in cells which have partly or altogether lost this ability, more preferably for restoration of the natural ability to undergo apoptosis in cancer cells which have fully lost this ability, most preferably in cancer cells showing a propensity to necrotic cell death, e.g. a propensity to necrotic cell death in reaction to immunological, physiological, chemical, physical or radiation-induced stress or damage.

Suitable compounds can be identified among the compounds of formula (I), physiologically acceptable salts or derivatives thereof, using well-known in vitro screening procedures such as high-throughput screening (HTS) procedures comprising testing the cellular readiness for apoptosis by each of a number of candidate compounds of formula (I), physiologically acceptable salts or derivatives thereof and identifying those which have the desired activity.

At a higher level of screening, the suitability for promoting readiness of apoptosis or induces apoptosis of cancer cells, in particular of gastric or colorectal cancer, may be investigated in vivo using animals model known to the skilled artisan.

In accordance with the present invention, treating gastric or colorectal cancer in a subject in need of such treatment comprises administering to said subject a therapeutically effective amount of one or more compound(s) of formula (I), a physiologically acceptable salt or solvate thereof.

The phrase "therapeutically effective" is intended to describe the amount of an agent required to achieve the objects of treatment as defined above in the course of the treatment.

The compounds of formula (I), physiologically acceptable salts or solvates thereof can be incorporated into standard pharmaceutical dosage forms when they are to be used as active ingredients in the uses of the present invention. This also includes any other chemotherapeutic agent applied in combination as described above. For the use according to the present invention, compounds of formula (I) or physiologically acceptable salts or solvates thereof and further chemotherapeutics may be formulated together in one pharmaceutical preparation. The present invention further contemplates separate formulations of said active ingredients which may be administered simultaneously, whereby even different dosage forms and routes may be applied. Besides such co-administration, the use of the present invention also contemplates dosing schedules, whereby the desired plasma level of the drugs involved is maintained in the treated subject even though the individual drugs combined for this treatment are not being administered simultaneously. The compounds and combinations of the invention can be administered in systemic or local, oral or parenteral applications. For this purpose, suitable pharmaceutical excipients, diluents and adjuvants, known to the skilled artisan, are incorporated in the pharmaceutical preparation(s) comprising, e.g., organic and inorganic inert carrier materials such as water, gelatine, lactose, starch, magnesium stearate, talc, vegetable oils, gums, polyalkylene glycols, etc. These pharmaceutical preparations can be employed in a solid form, e.g. as tablets, capsules, or in liquid form, e.g, as solutions, suspensions or emulsions. Pharmaceutical excipients and adjuvants which may be added include preservatives, antioxidants, antimicrobial agents and other stabilizers; wetting, emulsifying and suspending agents, and anti-caking compounds; fragrance and coloring additives; compositions for improving compressibility or agents to create a delayed, sustained or controlled release of the active ingredient; and various salts to change the osmotic pressure of the pharmaceutical preparation or to act as buffers. All these formulations including controlled-release forms to achieve relatively uniform dosing in particular for different drugs with varying half-lives are well within the skill of the artisan to devise and create.

The therapeutically effective amount of a compound of formula (I), a physiologically acceptable salt or solvate thereof, or a combination as defined above may be administered systemically to said subject, wherein said systemic administration comprises: (1) injection or infusion into suitable body tissues or cavities of a pharmaceutical composition containing said compound in suitable liquid form such as aqueous solutions, emulsions or suspensions for intraarterial, intra- or transdermal (including subcutaneous), and most commonly for intramuscular or intravenous delivery thereof; or for serving as a depot for delivery thereof; (2) instillation into suitable body tissues or cavities of a pharmaceutical composition containing said compound in suitable solid form, e.g., comprising a matrix of bio-compatible and bio-erodible materials in which particles of a solid compound of formula (I), a physiologically acceptable salt or solvate thereof, are dispersed, or in which, possibly, globules or isolated cells of a liquid compound of formula (I), a physiologically acceptable salt or solvate thereof, are entrapped, for serving as a solid implant composition for delayed-, sustained-, and/or controlled-release delivery thereof; or (3) ingestion or administration of a pharmaceutical composition containing said compound in suitable solid or liquid form for transdermal delivery thereof, for instance a transdermal patch or a subepidermal (subcuticular) implant, for peroral delivery thereof.

Said therapeutically effective amount of a compound of formula (I), a physiologically acceptable salt or solvate thereof as defined may also be administered locally to said subject, wherein said local administration comprises: (1) injection or infusion into a local site of a pharmaceutical composition containing said compound of formula (I), physiologically acceptable salt or solvate thereof in suitable liquid form for delivery thereof, including components which provide delayed-release, controlled-release, and/or sustained-release of said compound into said local site; or for serving as a depot for delivery thereof wherein said composition provides storage of said compound and thereafter delayed-, sustained-, and/or controlled-release thereof; or (2) instillation of a pharmaceutical composition containing said compound in suitable solid form for serving as a solid implant for delivery thereof, said composition optionally providing delayed-, sustained-, and/or controlled-release of said compound to said local site.

A dosage form described herein may be formulated so as to provide controlled-, sustained-, and/or delayed release of the active ingredient from said dosage form.

Preferred peroral dosage forms for systemic administration are solids, e.g. palatable oral compositions such as tablets, capsules, caplets, etc., and liquids, e.g. solutions, suspensions, emulsions, etc.

Injections may also be made of pharmaceutical compositions containing the compound of formula (I), a physiologically acceptable salt or solvate thereof, where the pharmaceutical composition is in delayed-release, controlled-release, or sustained-release form. These formulations of recognized composition may be solids, semi-solids, gels or other liquid/solid combinations in which an erodible matrix or series of coatings is used to provide a continuous release of the compound of formula (I), the physiologically acceptable salt or solvate thereof at a predetermined rate or at variable rates if desired. The terms "extended-release" and "long-acting" as well as others are used to describe these formulations. All of these employ various combinations of bioerodible polymers, e.g., various cellulosic polymers, and natural materials, e.g., corn starch and magnesium stearate, to obtain slow and/or uniform dispensing of the compound of formula (I), a physiologically acceptable salt or solvate thereof contained within the matrix.

The therapeutically effective amount of the compound of formula (I) is administered to a mammal to be treated in an amount expressed as milligrams per $m^2$ of body surface of said mammal, per day: "$mg/m^2/day$". The expression "per day" as used herein should not be interpreted as necessarily requiring that any particular dosage form be administered on a daily basis to the subject being treated. The expression "per day" is merely an indication of the smallest convenient but arbitrary segment of time which is being used as part of the overall unit for measuring the dose of effective compound being administered. Depending on the route of application and other details, the daily dosage may be split into a number of sub-doses for subsequent administration in regular intervals, or, when using sustained or controlled release, several daily dosages may be joined into a single depot dosage. The dose, i.e. the therapeutically effective amount of a compound of formula (I), will usually range from about 0.2 mg/m²/day to about 2000 mg/m²/day, preferably from about 0.5 mg/m²/day to about 1500 mg/m²/day, more preferably from about 1.0 mg/m²/day to about 1000 mg/m²/day. In case of a combination of a compound of formula (I) with a further chemotherapeutic agent such as an anticancer agent, administration may be simultaneously, for example given as co-formulation or separately, or sequentially. The dose of a compound of formula (I) will usually be as given above whereas the dose of the further chemotherapeutic agent will range from about 0.2 mg/m²/day to about 2000 mg/m²/day, preferably from about 0.5 mg/m²/day to about 1500 mg/m²/day, more preferably from about 1.0 mg/m²/day to about 1000 mg/m²/day. For determination of dosage, particularities of absorption, metabolism and excretion characteristic for the respective tumor type, or found in an individual subject, will have to be taken into account.

It is necessary for the skilled artisan, not only to determine the preferred route of administration and the corresponding dosage form and amount, but said artisan must also determine the dosing regimen, i.e., the frequency of dosing. In general terms it is most likely that the choice will be between once-a-day (s.i.d.) dosing and twice-a-day (b.i.d.) dosing, and that the former will provide more rapid and profound therapy, while the latter will provide less profound but more sustained therapy.

The skilled artisan will appreciate that treatment according to the present invention may also be combined with any suitable non-pharmacological treatment.

It is also contemplated that in accordance with the present invention there will also be provided a package suitable for use in commerce for treating gastric or colorectal cancer in a subject in need of such treatment, comprising a suitable outer carton and an inner container removably housed therein; enclosed in said container a suitable dosage form of a compound of formula (I), a physiologically acceptable salt or solvate thereof as described hereinabove; and associated with said carton or container printed instructional and informational material, which may be attached to said carton or to said container enclosed in said carton, or displayed as an integral part of said carton or container, said instructional and informational material stating in words which convey to a reader thereof that said active ingredient, when administered to a subject in a condition of gastric or colorectal cancer will ameliorate, diminish, actively treat, reverse or prevent the condition. In a preferred embodiment said package comprising carton and container as above-described will conform to all regulatory requirements relating to the sale and use of drugs for the treatment of subjects, including especially said instructional and informational material.

For diagnostic purposes, it may also be found expedient to perform in vitro testing, e.g. for determining the sensitivity of an individual gastric or colorectal growth to a treatment with a compound of formula (I), a physiologically acceptable salt or solvate thereof or composition containing the same, as defined above. For example, an appropriate sample obtained from the subject may be subjected to various concentrations of the compounds and/or compositions of the invention and the effect analyzed in one or more suitable assays. Apoptosis, inhibition of proliferation, reduction of viability, etc. can be measured in vitro by any of a number of methods well-known to a person skilled in the art. The data thus obtained may serve as a basis for rationally determining a favorable dosage and route of application for treatment of said individual gastric or colorectal adenocarcinoma.

The term "alkyl", "alkoxy", "alkylamino" etc. denotes chemical radicals which include linear or branched alkyl groups having 1 to 6 and preferably 1 to 4 carbon atoms. Examples for alkyl groups are methyl, ethyl, n-propyl, i-propyl, n-butyl, sec-butyl, iso-butyl, t-butyl, n-pentyl or n-hexyl. Examples for alkoxy groups are methoxy, ethoxy, n-propoxy, isopropoxy, n-butoxy. Halogen means F, Cl, Br and I, preferably F and Cl.

Heteroaryl means a 5- or 6-membered aromatic ring having 1 or 2 heteroatoms which are independently selected from O, N, and S. Examples for heteroaryl are thienyl, furyl, imidazolyl, pyrazolyl, thiazolyl, oxazolyl, pyridyl or pyrimidyl.

Heterocyclyl means a 5- or 6-membered saturated or unsaturated, non-aromatic ring having 1 or 2 heteroatoms which are independently selected from O, N, and S. Examples for heterocyclyl are pyrrolidinyl, tetrahydrofuranyl, imidazolinyl, imidazolidinyl, piperidinyl, morpholinyl, piperazinyl. In a particular embodiment heterocyclyl is piperidinyl, morpholinyl and piperazinyl. If heterocyclyl is substituted, the substituent may be at a carbon atom or at the additional nitrogen heteroatom. Examples for substituted heterocyclyl are 4-methylpiperazinyl or 2,2,6,6-tetramethylpiperidine.

Physiologically acceptable salts of the compounds of formula (I) include acid addition salts with inorganic acids, such as hydrochloric acid, sulfuric acid, or phosphoric acid, or with organic acids, in particular carboxylic acids, such as acetic acid, tartaric acid, lactic acid, citric acid, maleic acid, amygdalic acid, ascorbic acid, fumaric acid, gluconic acid or sulfonic acids, such as methane sulfonic acid, benzene sulfonic acid and toluene sulfonic acid. Physiologically acceptable solvates are in particular hydrates.

According to a one embodiment, the present invention relates to the use of compounds of formula (I) wherein $R^3$ is selected from:

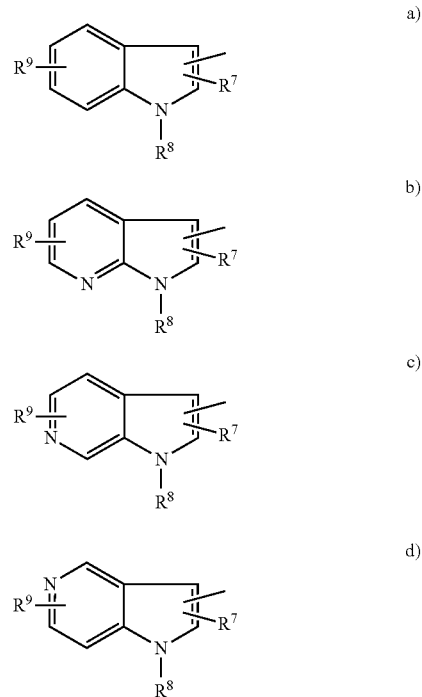

-continued

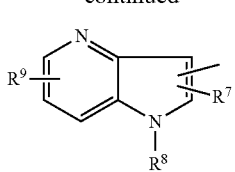
e)

wherein R⁷ is H, $C_1$-$C_6$-alkyl or phenyl,
R⁸ is H, $C_1$-$C_6$-alkyl or phenyl and
R⁹ is H, $C_1$-$C_6$-alkyl, $C_1$-$C_6$-alkoxy, OH, halogen, NH₂, $C_1$-$C_6$-alkylamino, di-$C_1$-$C_6$-alkylamino, heteroaryl with 5 or 6 ring atoms containing 1 or 2 heteroatoms which are independently selected from O, N, and S, or heterocyclyl with 5 or 6 ring atoms containing 1 or 2 heteroatoms which are independently selected from O, N, and S.

According to a further embodiment, the present invention relates to the use of compounds of formula (I) wherein R² is a phenyl group which is substituted with 3 $C_1$-$C_6$-alkoxy groups and R³ is selected from:

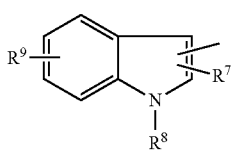
a)

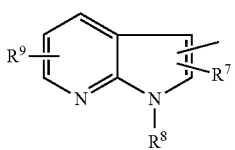
b)

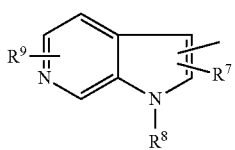
c)

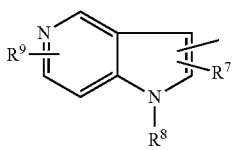
d)

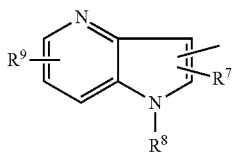
e)

wherein R⁷ is H or $C_1$-$C_6$-alkyl,
R⁸ is H or $C_1$-$C_6$-alkyl-R¹⁰, wherein R¹⁰ is selected from:
a) amino,
b) $C_1$-$C_6$-alkylamino,
c) di-$C_1$-$C_6$-alkylamino,
d) hydroxy,
e) $C_1$-$C_6$-alkoxy,
f) saturated heterocyclyl with 5 or 6 ring atoms containing a nitrogen heteroatom and optionally 1 or 2 additional heteroatoms which are independently selected from O, N and S, wherein the heterocyclyl is attached to the $C_1$-$C_6$-alkyl group via the nitrogen atom and may carry one, two, three or four $C_1$-$C_6$-alkyl substituents;
g) phenoxy,
h) benzyloxy,
i) R¹¹CONR¹²—,
j) NR¹²R¹²CO—,
k) $C_1$-$C_6$-alkyl-NHCONH—,
l) $C_1$-$C_6$-alkyl-NHCOO—,
m) $C_1$-$C_6$-alkyl-OCONH—,
n) R¹²—OSO₂O—,
o) R¹¹SO₂O—,
p) R¹²—OSO₂—,
q) R¹¹SO₂—,
r) (R¹²O)₂P(O)O—,
s) (R¹²O)₂P(O)—, and
t) (R¹²O)R¹¹P(O)O—;

R⁹ is H, $C_1$-$C_6$-alkyl, $C_1$-$C_6$-alkoxy, OH, or halogen,
R¹¹ is $C_1$-$C_6$-alkyl; and R¹² is $C_1$-$C_6$-alkyl.

According to a further particular embodiment, the present invention relates to the use compounds of formula (I) wherein R² is a group having the formula

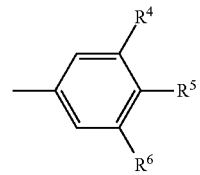

wherein R₄, R₅ and R₆ are $C_1$-$C_6$-alkoxy.

According to a further particular embodiment, the present invention relates to the use compounds of formula (I) wherein R¹ is H.

According to one embodiment, the present invention relates to the use of compounds of formula (Ia)

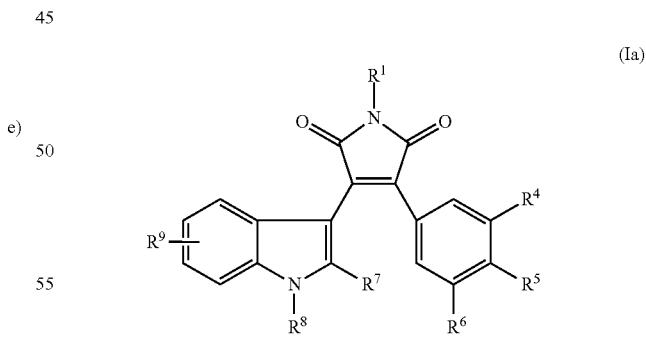
(Ia)

wherein R¹ is as defined in claim 1, R⁴, R⁵ and R⁶ are $C_1$-$C_6$-alkoxy groups and R⁷, R⁸ and R⁹ are as defined in claim 2 or 3.

According to a further particular embodiment, the present invention relates to the use compounds of formula (I) wherein R¹, R⁷ and R⁸ are H and R⁹ is halogen.

According to a further embodiment, the present invention relates to the use of compounds of formula (Ib)

(Ib)

wherein R¹ is as defined in claim 1, R⁴, R⁵ and R⁶ are C₁-C₆-alkoxy groups and R⁷, R⁸ and R⁹ are as defined in claim 2 or 3.

According to a further embodiment, the present invention relates to the use of compounds of formula (Ic)

(Ic)

wherein R¹ is as defined in claim 1, R⁴, R⁵ and R⁶ are C₁-C₆-alkoxy groups and R⁷, R⁸ and R⁹ are as defined in claim 2 or 3.

According to a further embodiment, the present invention relates to the use of compounds of formula (Id)

(Id)

wherein R¹ is as defined in claim 1, R⁴, R⁵ and R⁶ are C₁-C₆-alkoxy groups and R⁷, R⁸ and R⁹ are as defined in claim 2 or 3.

According to a further embodiment, the present invention relates to the use compounds of formula (Ie)

(Ie)

wherein R¹ is as defined in claim 1, R⁴, R⁵ and R⁶ are C₁-C₆-alkoxy groups and R⁷, R⁸ and R⁹ are as defined in claim 2 or 3.

According to a further particular embodiment, R⁷, R⁸ and R⁹ are H.

According to a further particular embodiment, R¹, R⁷ and R⁹ are H.

According to a further particular embodiment, R¹⁰ is selected from:
a) amino,
b) C₁-C₆-alkylamino,
c) di-C₁-C₆-alkylamino,
d) hydroxy,
e) C₁-C₆-alkoxy,
f) saturated heterocyclyl with 5 or 6 ring atoms containing a nitrogen heteroatom and optionally 1 or 2 additional heteroatoms which are independently selected from O, N and S, wherein the heterocyclyl is attached to the C₁-C₆-alkyl group via the nitrogen atom and may carry one, two, three or four C₁-C₆-alkyl substituents.

According to a further embodiment, R¹⁰ is selected from
a) amino,
b) C₁-C₆-alkylamino,
c) di-C₁-C₆-alkylamino,
d) hydroxy, and
e) C₁-C₆-alkoxy.

According to a further embodiment, R¹⁰ is selected from
a) amino,
b) C₁-C₆-alkylamino, and
c) di-C₁-C₆-alkylamino.

According to a further embodiment, R¹⁰ is selected from
d) hydroxy, and
e) C₁-C₆-alkoxy.

According to a further embodiment, R¹⁰ is
f) saturated heterocyclyl with 5 or 6 ring atoms containing a nitrogen heteroatom and optionally 1 or 2 additional heteroatoms which are independently selected from O, N and S, wherein the heterocyclyl is attached to the C₁-C₆-alkyl group via the nitrogen atom and may carry one, two, three or four C₁-C₆-alkyl substituents.

According to a further embodiment, R¹⁰ is selected from
g) phenoxy, and
h) benzyloxy.

According to a further embodiment, R¹⁰ is selected from
i) R¹¹CONR¹²—, and
j) NR¹²R¹²CO—.

According to a further embodiment, R¹⁰ is selected from
k) C₁-C₆-alkyl-NHCONH—,
l) C₁-C₆-alkyl-NHCOO—, and
m) C₁-C₆-alkyl-OCONH—.

According to a further embodiment, R¹⁰ is selected from
n) R¹²—OSO₂O—,
o) R¹¹SO₂O—,
p) R¹²—OSO₂—, and
q) R¹¹SO₂—.

According to a further embodiment, R¹⁰ is selected from
r) (R¹²O)₂P(O)O—,
s) (R¹²O)₂P(O)—, and
t) (R¹²O)R₁₁P(O)O—.

Particular compounds of formula (I) include the compounds of Table 1:

TABLE 1

| Compound Name | Compound Structure | herein also referred to as: |
|---|---|---|
| 3-(1H-indol-3-yl)-4-(3,4,5-trimethoxyphenyl)-maleinimid | 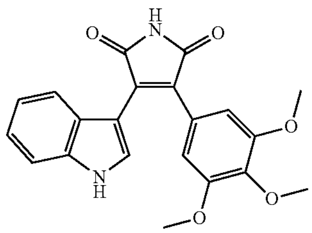 [SMILES: COc1cc(C2=C(c3c[nH]c4ccccc34)C(=O)NC2=O)cc(OC)c1OC] | A |
| 3-(7-Azaindol-3-yl)-4-(3,4,5-trimethoxyphenyl)-maleinimid | 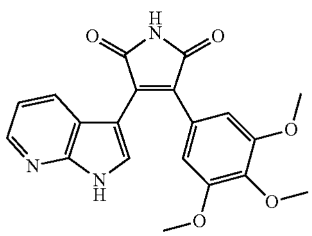 | B |
| 3-(6-Azaindol-3-yl)-4-(3,4,5-trimethoxyphenyl)-maleinimid | 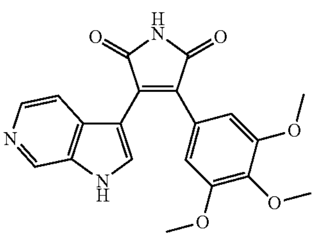 [SMILES: COc1cc(C2=C(c3c[nH]c4cnccc34)C(=O)NC2=O)cc(OC)c1OC] | C |
| 3-(5-Azaindol-3-yl)-4-(3,4,5-trimethoxyphenyl)-maleinimid | 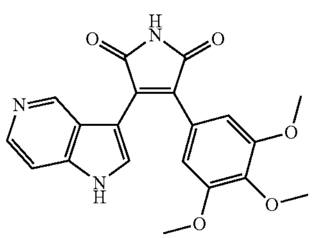 [SMILES: COc1cc(C2=C(c3c[nH]c4ccncc34)C(=O)NC2=O)cc(OC)c1OC] | D |
| 3-(4-Azaindol-3-yl)-4-(3,4,5-trimethoxyphenyl)-maleinimid | 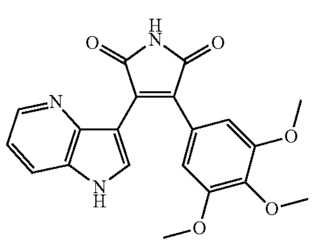 [SMILES: COc1cc(C2=C(c3c[nH]c4cccnc34)C(=O)NC2=O)cc(OC)c1OC] | E |
| 3-(1-[2-Ammonioethyl]-1H-indol-3-yl)-4-(3,4,5-trimethoxyphenyl)-maleinimid-chlorid | 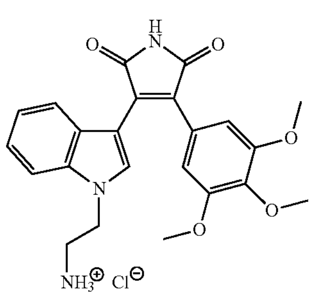 [SMILES: COc1cc(C2=C(c3cn(CC[NH3+])c4ccccc34)C(=O)NC2=O)cc(OC)c1OC ; [Cl-]] | F |
| 3-(1-[3-Ammoniopropyl]-1H-indol-3-yl)-4-(3,4,5-trimethoxyphenyl)-maleinimid-chlorid | | G |
| 3-(1-[2-Hydroxyethyl]-1H-indol-3-yl)-4-(3,4,5-trimethoxyphenyl)-maleinimid | | H |
| 3-(1-[3-Hydroxypropyl]-1H-indol-3-yl)-4-(3,4,5-trimethoxyphenyl)-maleinimid | | I |
| 3-{1-[2-(Dimethylamino)ethyl]-1H-indol-3-yl}-4-(3,4,5-trimethoxyphenyl)-maleinimid | | J |
| 3-{1-[3-(Dimethylamino)propyl]-1H-indol-3-yl}-4-(3,4,5-trimethoxyphenyl)-maleinimid | | K |

TABLE 1-continued

| Compound Name | Compound Structure | herein also referred to as: |
|---|---|---|
| 3-{1-[2-(Piperidin-1-yl)ethyl]-1H-indol-3-yl}-4-(3,4,5-trimethoxyphenyl)-maleinimid | 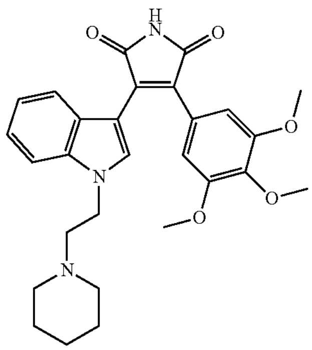 [SMILES: COc1cc(C2=C(c3cn(CCN4CCCCC4)c4ccccc34)C(=O)NC2=O)cc(OC)c1OC] | L |
| 3-{1-(2-Morpholinoethyl)-1H-indol-3-yl}-4-(3,4,5-trimethoxyphenyl)-maleinimid | 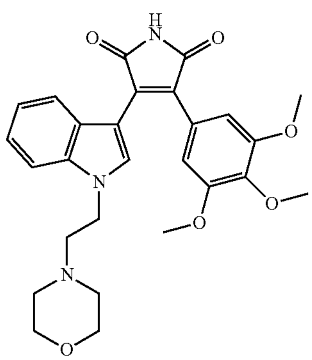 [SMILES: COc1cc(C2=C(c3cn(CCN4CCOCC4)c4ccccc34)C(=O)NC2=O)cc(OC)c1OC] | M |
| 3-{1-[3-(4-Methylhexahydro-1-pyrazindiimyl)propyl]-1H-indol-3-yl}-4-(3,4,5-trimethoxyphenyl)-maleinimiddichlorid | 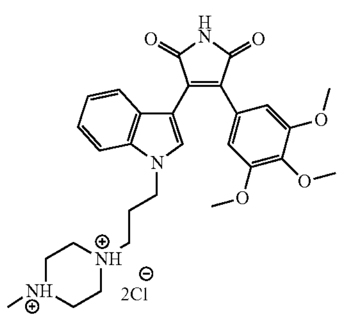 | N |
| 3-(5-Fluor-1H-indol-3-yl)-4-(3,4,5-trimethoxyphenyl)-maleinimid | 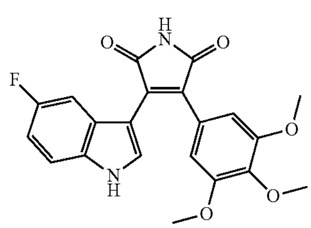 [SMILES: COc1cc(C2=C(c3c[nH]c4ccc(F)cc34)C(=O)NC2=O)cc(OC)c1OC] | O |
| 3-(5-Brom-1H-indol-3-yl)-4-(3,4,5-trimethoxyphenyl)-maleinimid | 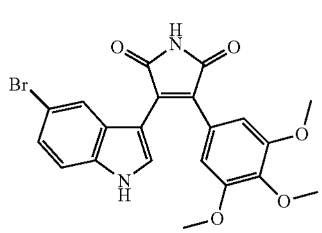 [SMILES: COc1cc(C2=C(c3c[nH]c4ccc(Br)cc34)C(=O)NC2=O)cc(OC)c1OC] | P |

A further embodiment of the invention is a combination of the compounds of formula I with a further chemotherapeutic agent as defined above.

The compounds of the present invention can be prepared according to known methods, for example according to the methods, which are disclosed in WO 02/38561, EP 328 026, WO 03/095452, WO 03/103663 and WO 2006/061212. For the purposes of the present invention a modified procedure reported in *Tetrahedron Letters* (1999) 40: 1109-1112 has been proven to be particularly efficient. This procedure can be illustrated by the following reaction sequence:

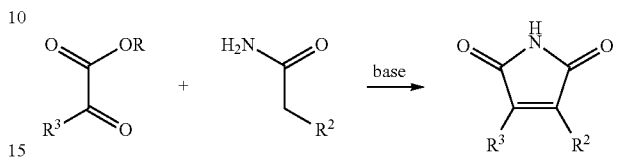

An indole glyoxyl ester is reacted with a phenyl acetamide derivative in a one-pot reaction in an inert solvent in the presence of a strong base. Preferably an ether is used as an inert solvent, such as tetrahydrofurane or dioxane. As a base potassium t-butoxide can for example be used. The water formed during the reaction is removed, for example by using a molecular sieve. The phenyl acetamides used as starting material are readily available from the corresponding acetic acids which are converted to the acid chloride and hydrolyzed with ammonia. The indole glyoxyl esters (R=methyl, ethyl) were synthesized by Friedel-Crafts-type acylation of the corresponding indole derivative with methyl or ethyl oxalyl chloride, cf. *Tetrahedron* 1999, 55 (43), 12577-12594. The corresponding azaindole glyoxyl esters can be prepared according to the method reported in *J. Org. Chem.* 2002, 67, 6226-6227 or by Friedel-Crafts acylation in the presence of aluminum chloride, cf. *Organic Letters* (2000) vol. 2, no. 10, 1485-1487. The 4- and 6-azaindole starting compounds can be prepared by reacting 2-chloro-3-nitropyridine or 3-nitro-4-chloropyridine with vinyl magnesium bromide to give the 7-chloro-substituted 4- or 6-azaindole. The chloro substituent is then removed by catalytic hydrogenation. Said reactions are carried out as described in *J. Org. Chem.* 67, 2345-2347 (2002) and *J. Heterocycl. Chem.* 29, 359-363 (1992). The 4-azaindole starting compound can also be synthesized according to the procedures disclosed in Org. Biomol. Chem. 3, 20, 3701-3706 (2005).

The 5- and 7-azaindole starting compounds can be prepared by reacting 2- or 4-aminopyridine with di-tert-butyldicarbonate to 2- or 4-t-butoxycarbonylaminopyridine which is then reacted with methyl iodide and dimethylformamide in the presence of t-butyl lithium. The obtained product is then treated with a strong acid to give 5- or 7-azaindole. Said reactions are described in *Synthesis* 7, 877-882 (1996).

In order to further demonstrate the uses, methods and compositions of the present invention, there is presented in the paragraphs which follow specific descriptive examples of typical procedures which may be employed in carrying out said methods. However, said examples are intended to be illustrative only and should not be taken as in any way a limitation of the present invention, for which purpose the present claims are appended hereto.

EXAMPLES

General Procedure for the Preparation of 3-(indolyl)- and a 3-(azaindolyl)-4-phenylmaleimide Derivatives The compounds herein referred to as A, B, C, and D and their preparation are disclosed in WO2006/061212. Compounds E to P are prepared according to the following examples:

Infrared spectra were recorded on a Thermo Nicolet Avatar 330 FT-IR spectrometer. 1H (300 MHz, digital resolution 0.3768 Hz) and 13C (75 MHz, digital resolution 1.1299 Hz) NMR were recorded on a Bruker AC 300: the data are reported as follows: chemical shift in ppm from Me$_4$Si as external standard, multiplicity and coupling constant (Hz). EI-Mass spectra were recorded on a Varian MAT 44S (80 eV) and FD-Mass spectra on a Finnigan MAT 7 (5 kV). For clarity only the highest measured signal is given for FD-Mass spectra. Elemental analyses were performed on a Haereus CHN rapid, Carlo Erba Strumentazione 1106. Combustion analyses agreed with the calculated data within ±0.4 unless otherwise stated. Melting points/decomposition temperatures were determined on a Büchi apparatus according to Dr. Tottloi and are uncorrected. Where appropriate, column chromatography was performed for crude precursors with Merck silica gel 60 (0.063-0.200 mm). Column chromatography for test compounds was performed using a MPLC-System B-680 (Büchi) with Merck silica gel (0.015-0.040 mm). The progress of the reactions was monitored by thin layer chromatography (TLC) performed with Merck silica gel 60 F-254 plates. Where necessary, reactions were carried out in a nitrogen atmosphere using 4 Å molecular sieves. All reagents and solvents were obtained from commercial sources and used as received.

Example E 3-(4-Azaindol-3-yl)-4-(3,4,5-trimethoxyphenyl)-1H-pyrrol-2,5-dione

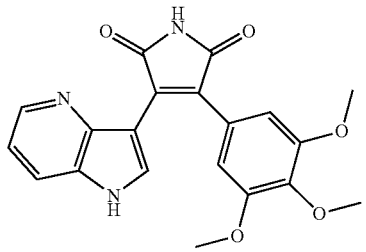 [SMILES: COc1cc(C2=C(c3c[nH]c4cccnc34)C(=O)NC2=O)cc(OC)c1OC]

(a) Dimethyl-2-(3-nitropyridin-2-yl)malonate

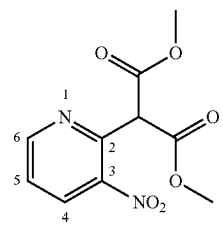 [SMILES: COC(=O)C(C(=O)OC)c1ncccc1[N+](=O)[O-]]

A modified procedure of Cash et al. (Org. Biomol. Chem. 2005, 3, 3701-3706) was used. 2-Chloro-3-nitropyridine (2 g, 12.5 mmol) was added to a stirred suspension of NaH (0.5 g, 12.5 mmol; mixture of 60% NaH mineral oil) in 20 ml dry DMF under nitrogen. Dimethyl-malonate (1.43 ml, 1.65 g, 12.5 mmol) was cautiously added dropwise. After the reaction was stirred for 5 h at room temperature, the solution was diluted with water. After adding diethylether the mixture was washed with saturated NaCl solution for four times to remove the DMF. The organic phase was dried over Na$_2$SO$_4$, filtered, concentrated and purified by column chromatography (petrolether:ethylacetate 2:1). Dimethyl-2-(3-nitropyridin-2-yl)malonate was obtained as a pale brown oil (1.4 g, 5.5 mmol=44%). $^1$H NMR (300 MHz, CDCl$_3$) 8.83 (pdd; $^3$J=1.3 Hz; $^3$J=4.7 Hz; 1H; H-6); 8.49 (pdd; $^3$J=1.3 Hz; $^3$J=8.3 Hz; 1H; H-4); 7.54 (pdd; $^3$J=4.7 Hz; $^3$J=8.3 Hz; 1H; H-5); 5.56 (s; 1H; CH); 3.83 (s; 6H; OCH$_3$).

(b) 2-Methyl-3-nitropyridine

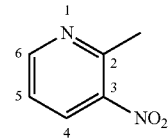

A modified procedure of Cash et al. (Org. Biomol. Chem. 2005, 3. 3701-3706) was used. Dimethyl-2-(3-nitropyridin-2-yl)malonate (1.4 g, 5.5 mmol) was dissolved in 70 ml 6 M HCl and refluxed for 8 h. After neutralization with saturated Na$_2$CO$_3$ solution the solution was extracted three times with dichloromethane. The combined organic layers were dried over Na$_2$SO$_4$, filtered, concentrated and purified by bulb tube distillation (0.35 mbar; 70-80° C.). 2-Methyl-3-nitropyridine (0.7 g, 5.1 mmol, 92%) was obtained as a pale yellow oil. $^1$H NMR (300 MHz, CDCl$_3$) 8.72 (pdd; $^3$J=1.2 Hz; $^3$J=4.7 Hz; 1H; H-6); 8.27 (pdd; $^3$J=1.2 Hz; $^3$J=8.2 Hz; 1H; H-4); 7.35 (pdd; $^3$J=4.7 Hz; $^3$J=8.2 Hz; 1H; H-5); 2.86 (s; 3H; CH$_3$).

(c) (E)-N,N-Dimethyl-2-(3-nitropyridin-2-yl)ethenamine

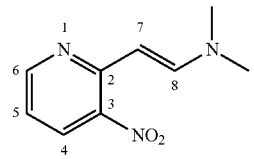

A modified procedure of Cash et al. (Org. Biomol. Chem. 2005, 3. 3701-3706) was used. 2-Methyl-3-nitropyridine (0.7 g, 5.1 mmol) was dissolved in 15 ml dry DMF and stirred under nitrogen. Dimethylformamiddimethylacetal (DMF-DMA) (1.35 ml, 1.22 g, 10.2 mmol) was added dropwise. The reaction was heated to 90° C. for 4 h. After approximately 15 min a deep redish color appeared. After evaporating the solvent (E)-N,N-Dimethyl-2-(3-nitropyridin-2-yl)ethenamine is obtained as a red oil (0.16 g, 0.8 mmol, 73%) which can be used without further purification. $^1$H NMR (300 MHz, CDCl$_3$) 8.40 (pdd; $^3$J=1.7 Hz; $^3$J=4.4 Hz; 1H; H-6); 8.16 (pdd; $^3$J=1.7 Hz; $^3$J=8.3 Hz; 1H; H-4); 8.04 (d; $^3$J$_{AX}$=12.5 Hz; 1H; H-8); 6.76 (pdd; $^3$J=4.4 Hz; $^3$J=8.3 Hz; 1H; H-5); 6.15 (d; $^3$J$_{AX}$=12.5 Hz; 1H; H-7); 3.01 (s; 6H; CH$_3$).

(d) 4-Azaindole

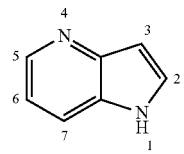

A modified procedure of Cash et al. (Org. Biomol. Chem. 2005, 3. 3701-3706) was used. 0.2 g of 10% Pd/C was flashed with nitrogen before 10 ml of a mixture of 8.8% formic acid in methanol was added cautiously. The crude (E)-N,N-Dimethyl-2-(3-nitropyridin-2-yl)ethenamine obtained as a red oil (0.69 g, 3.6 mmol) was also dissolved in 10 ml of a mixture of 8.8% formic acid in methanol before it was added to the reaction. The reaction was stirred for 4 h until the red color completely disappeared. The Pd catalyst was removed by filtration through Celite®, the filtrate was concentrated. After sitting over night, the product, 4-azaindole, crystallized (0.21 g, 1.8 mmol, 71%). $^1$H NMR (300 MHz, CDCl$_3$) 9.00 (bs; 1H; NH); 8.48 (pdd; $^4$J=1 Hz; $^3$J=4.6 Hz; 1H; H-5); 7.70 (pdd; $^4$J=1 Hz; $^3$J=8.2 Hz; 1H; H-7); 7.48 (pt; $^3$J=2.9 Hz; 1H; H-2); 7.12 (pdd; $^3$J=4.6 Hz; $^3$J=8.2 Hz; 1H; H-6); 6.76 (m; 1H; H-3).

(e) Ethyl-2-(4-azaindol-3-yl)-2-oxoacetate

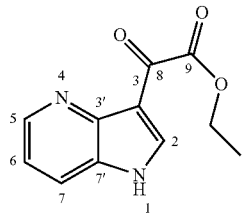 [SMILES: CCOC(=O)C(=O)c1c[nH]c2cccnc12]

Aluminium chloride (3.1 g, 23 mmol) and 4-azaindole (0.38 g, 4.6 mmol) were stirred in 100 ml dry dichloromethane at room temperature under nitrogen atmosphere. After 30 min ethoxalylchloride (2.5 ml, 3.0 g, 23 mmol) was added dropwise. The reaction mixture was stirred over night and then carefully hydrolyzed with ethanol/ice. After addition of dichloromethane the organic layer was separated, washed with NaHCO$_3$ solution, dried over Na$_2$SO$_4$, filtered and concentrated. After sitting over night ethyl-2-(4-azaindol-3-yl)-2-oxoacetate (0.5 g, 2.3 mmol, 50%) crystallized as a pale yellow powder. $^1$H NMR (300 MHz, CDCl$_3$) 12.21 (bs; 1H; NH); 8.58 (s; 1H; H-2); 8.49 (pdd; $^3$J=4.6 Hz; $^4$J=1.3 Hz; 1H; H-5); 7.93 (pdd; $^3$J=8.2 Hz; $^4$J=1.3 Hz; 1H; H-7); 7.27 (pdd; $^3$J=8.2 Hz; $^3$J=4.6 Hz; 1H; H-6); 4.37 (q; $^3$J=7.1 Hz; 2H; CH$_2$); 1.31 (t; $^3$J=7.1 Hz; 3H; CH$_3$).

(f) Ethyl-2-[1-(tert.-butoxycarbonyl)-4-azaindol-3-yl]-2-oxoacetate

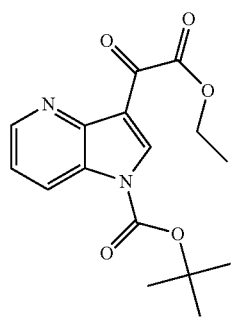 [SMILES: CCOC(=O)C(=O)c1cn(C(=O)OC(C)(C)C)c2cccnc12]

Di-tert.-butyldicarbonate (0.48 g, 2.2 mmol) and a catalytic amount of DMAP were added to a stirred solution of ethyl-2-(4-azaindol-3-yl)-2-oxoacetate (0.48 g, 2.2 mmol) in 10 ml dichloromethane. After 2 h the solvent was evaporated and the residue was purified by column chromatography to yield ethyl-2-[1-(tert.-butoxycarbonyl)-4-azaindol-3-yl]-2-oxoacetate (0.6 g, 1.9 mmol, 86%) as pale yellow crystals. $^1$H NMR (300 MHz, CDCl$_3$) 8.86 (s; 1H; H-2); 8.72 (pdd; $^4$J=1.4 Hz; $^3$J=4.7 Hz; 1H; H-5); 8.42 (pdd; $^4$J=1.4 Hz; $^3$J=8.4 Hz; 1H; H-7); 7.32 (pdd; $^3$J=4.7 Hz; $^3$J=8.4 Hz; 1H; H-6); 4.45 (q; J=7.1 Hz; 2H; CH$_2$); 1.70 (s; 9H; C(CH$_3$)$_3$); 1.43 (t; $^3$J=7.1 Hz; 3H; CH$_3$).

(g) 3-(4-Azaindol-3-yl)-4-(3,4,5-trimethoxyphenyl)-1H-pyrrol-2,5-dione

A stirred solution of 3,4,5-trimethoxyphenylacetamide (0.38 g, 1.7 mmol) and ethyl-2-[1-(tert.-butoxycarbonyl)-4-azaindol-3-yl]-2-oxoacetate (0.54 g, 1.7 mmol) in dry THF (tetrahydrofurane) containing 15 g molecular sieve (4 Å) was cooled to 0° C. under nitrogen. At this temperature 1.0 M tert.-BuOK (3.7 ml, 3.62 mmol) was added via septum and the mixture was allowed to warm to room temperature. After stirring over night, the reaction was again cooled to 0° C. and quenched with saturated NH$_4$Cl-solution. The residue was filtered, extracted with ethylacetate and the combined organic layers were dried over Na$_2$SO$_4$, concentrated and purified by column chromatography (ethylacetate:ethanol 9:1). 3-(4-azaindolyl)-4-(3,4,5-trimethoxyphenyl)-maleinimide was obtained as yellow crystals (0.17 g, 0.45 mmol, 26%). Mp=274-275° C. IR $\tilde{\nu}$ [cm$^{-1}$]=3338; 2946; 1716. EI-MS m/z (rel. int.)=380.75 (1.37%; M$^{+•}$); 379.79 (25.54%); 378.79 (71.14%); $^1$H NMR (300 MHz, DMSO) 11.98 (bs; 1H; azaindole-NH); 11.14 (bs; 1H; imide-NH); 8.12 (pdd; $^4$J=1.0 Hz; $^3$J=4.6 Hz; 1H; H-5); 8.04 (pd; $^3$J=2.7 Hz; 1H: H-2); 7.83 (pdd; $^4$J=1.0 Hz; $^3$J=8.2 Hz; 1H; H-7); 7.09 (pdd; $^3$J=4.6 Hz; $^3$J=8.2 Hz; 1H; H-6); 6.87 (s; 2H; Ar—H); 3.62 (s; 3H; OCH$_3$); 3.32 (s; 6H; OCH$_3$)

General Procedure 1 for the Preparation of N–1 Substituted Indole-3-Ethylglyoxylate A modified procedure of Faul et al., *J. of Organic Chemistry* 1998, 63, 6, 1961-1973 and Zhang et Al., *Bioorg. Med. Chem. Lett.*, 2004, 14, 12, 3245-3250 was used. A stirred suspension of indole-3-ethylglyoxylate (1 equiv.), CsCO$_3$ or K$_2$CO$_3$ (1.3 equiv.) and the corresponding aliphatic bromo- or chloro-substituent in dry DMF was heated to 75-80° C. under nitrogen for 8 hours. The reaction was cooled to RT, diluted with ethyl acetate (40 ml) and filtered over Celite®. The mixture was washed with water (4×40 ml). The organic phase was dried over Na$_2$SO$_4$, filtered, concentrated and purified by column chromatography.

General Procedure 2 for the Preparation of 3-Phenyl-4-Indolyl-Maleinimides

The procedure of Peifer et al., WO 2006/061212 and *J. Med. Chem.* 2006, 49, 4, 1271-1281, was used to prepare 3-phenyl-4-indolyl-maleinimides.

Example F 3-(1-[2-Ammonioethyl]-1H-indol-3-yl)-4-(3,4,5-trimethoxyphenyl)-maleinimide-chloride

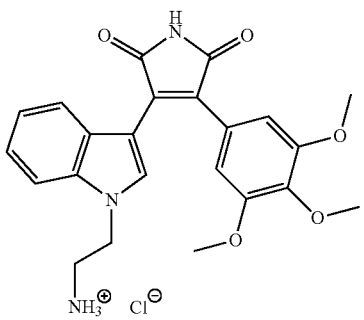 [SMILES: COc1cc(C2=C(c3cn(CC[NH3+])c4ccccc34)C(=O)NC2=O)cc(OC)c1OC ; [Cl-]]

A modified procedure of Wescott et al., *J. Org. Chem.* 2003, 68, 26, 10058-10066, was used to prepare tert.-butyl 2-bromoethylcarbamate. A solution of NaHCO$_3$ (24.4 mmol; 2.0 g) in 80 ml water and a solution of di-tert.-butyldicarbonate (24.4 mmol; 5.33 g) in 50 ml were added to a stirred suspension of 2-bromoethylammonium-bromide (24.4 mmol; 5.0 g) in 100 ml chloroform. The reaction was refluxed for 5 hours. After cooling to RT (room temperature) the organic phase was separated and aqueous phase was extracted with chloroform. The combined organic layers were dried over Na$_2$SO$_4$, filtered, concentrated and purified by column chromatography. Tert.-butyl 2-bromoethylcarbamate (6.86 mmol, 28.2%) was obtained as a colorless oil. $^1$H NMR (300 MHz, CDCl$_3$) 4.98 (bs; 1H; NH); 3.52 (dd; J=5.3 Hz; J=11.0 Hz; 2H; CH$_2$N); 3.44 (t; J=5.3 Hz; 2H; CH$_2$Br); 1.43 (s; 9H; C(CH$_3$)$_3$).

The general procedure 1 was then followed using the above product (6.68 mmol, 1.54 g), ethyl-2-(1H-indol-3-yl)-2-oxoacetate (6.68 mmol, 1.45 g) and Cs$_2$CO$_3$ (9.82 mmol, 3.20 g). The purification was achieved by column chromatography (petrol-ether:ethylacetate:diethylamine 5:4:1) to yield ethyl-2-(1-{2-[(tert.-butoxycarbonyl)-amino]ethyl}-1H-indol-3-yl)-2-oxoacetate (4.54 mmol, 68%) as white crystals. Mp=114-115° C. IR ṽ [cm$^{-1}$]=3357; 2977; 1727; 1686; 1638; 1518. EI-MS (m/z)=360 (7.59%; M$^{+\cdot}$). $^1$H NMR (300 MHz, CDCl$_3$) 8.44 (m; 1H; indole-H); 8.34 (s; 1H; indole-H); 7.42 (m; 1H; indole-H); 7.35 (m; 1H; indole-H); 4.63 (bs; 1H; NH); 4.37 (m; 4H; OC$\underline{H}_2$CH$_3$; indole-CH$_2$); 3.54 (q; $^3$J=6.2 Hz; 2H; CH$_2$—N); 1.43 (t; 3H; $^3$J=7.1 Hz; OC$\underline{H}_2$CH$_3$); 1.43 (s; 9H; C(CH$_3$)$_3$).

The general procedure 2 was then followed using ethyl-2-(1-{2-[(tert.-butoxycarbonyl)amino]ethyl}-1H-indol-3-yl)-2-oxoacetate (2 mmol, 0.77 g), 3,4,5-trimethoxyphenylacetamide (1.8 mmol, 0.41 g) and 1 M tert.-BuOK (6 mmol, 6 ml). The purification was achieved by column chromatography (petrolether:ethylacetate 4:6) to yield 3-(1-{2-[(tert.-butoxycarbonyl)amino]ethyl}-1H-indol-3-yl)-4-(3,4,5-trimethoxyphenyl)-maleinimide (0.8 mmol, 43%) as orange crystals. Mp 97-98° C. IR ṽ [cm$^{-1}$]=3300; 2987; 1698. EI-MS m/z (rel. int.)=521 (91.98%; M$^{+\cdot}$). $^1$H NMR (300 MHz, CDCl$_3$) 7.92 (s; 1H; indole-H); 7.36 (m; 1H; indole-H); 7.35 (bs; 1H; imide-NH); 7.17 (t; $^3$J=7.2 Hz; 1H; indole-H); 6.86 (t; $^3$J=7.2 Hz; 1H; indole-H); 6.78 (s; 2H; 2×Ar—H); 6.46 (d; $^3$J=8.1 Hz; 1H; indole-H); 4.63 (bs; 1H; NH); 4.36 (t; $^3$J=5.78 Hz; 2H; indole-CH$_2$); 3.86 (s; 3H; OCH$_3$); 3.55 (m; 2H; CH$_2$N); 3.49 (s; 6H; 2×OCH$_3$); 1.44 (s; 9H; C(CH$_3$)$_3$).

A stirred solution of 3-(1-{2-[(tert.-butoxycarbonyl)amino]ethyl}-1H-indol-3-yl)-4-(3,4,5-trimethoxyphenyl)-maleinimide (0.8 mmol, 0.4 g) in 50 ml ethanol and 2.3 M ethanolic HCl (3.42 mmol, 1.5 ml) was heated to 80° C. for 3 hours. The precipitate was filtered and washed with ethanol to give the title compound (0.66 mmol, 86%) as red crystals. Mp 277.1° C. IR ṽ [cm$^{-1}$]=3151; 2977; 1698. FD-MS m/z (rel. int.)=423.5 (1.2%; M$^{+\cdot}$). $^1$H NMR (300 MHz, CDCl$_3$) 11.12 (bs; 1H; imide-NH); 8.14 (bs; 3H; NH$_3$); 8.10 (s; 1H; indole-H); 7.63 (d; $^3$J=8.2 Hz; 1H; indole-H); 7.18 (t; $^3$J=7.3 Hz; 1H; indole-H); 6.82 (t; $^3$J=7.3 Hz; 1H; indole-H); 6.73 (s; 2H; 2×Ar—H); 6.38 (d; $^3$J=8.2 Hz; 1H; indole-H); 4.55 (t; $^3$J=6.6 Hz; 2H; indole-CH$_2$); 3.66 (s; 3H; OCH$_3$); 3.38 (s; 6H; 2×OCH$_3$); 3.25 (m; 2H; CH$_2$N). Anal. calcd for C$_{23}$H$_{24}$ClN$_3$O$_5$: C, 60.33; H, 5.28; N, 9.18. Found: C, 60.36; H, 5.29; N, 9.09.

Example G

3-(1-[3-Ammoniopropyl]-1H-indol-3-yl)-4-(3,4,5-trimethoxyphenyl)-maleinimide-chloride

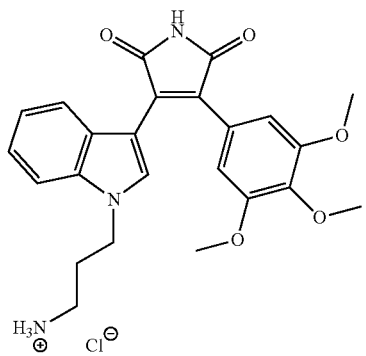 [SMILES: COc1cc(C2=C(c3cn(CCC[NH3+])c4ccccc34)C(=O)NC2=O)cc(OC)c1OC ; [Cl-]]

Tert.-butyl-(3-bromopropyl)carbamate (7.14 mmol, 78%) was synthesized using the same procedure as for example 1. $^1$H NMR (300 MHz, CDCl$_3$) 4.73 (bs, 1H; NH); 3.41 (t; $^3$J=6.5 Hz; 2H; CH$_2$Br); 3.24 (m; 2H; CH$_2$N); 2.02 (quint; $^3$J=6.5 Hz; 2H; CH$_2$C$\underline{H}_2$CH$_2$); 1.41 (s; 9H; C(CH$_3$)$_3$).

The general procedure 1 was then followed using the above product (7.14 mmol, 1.7 g), ethyl-2-(1H-indol-3-yl)-2-oxoacetate (4.6 mmol, 1.0 g) and Cs$_2$CO$_3$ (9.21 mmol, 3.0 g). The purification was achieved by column chromatography (petrol-ether:ethylacetate 1:1) to yield ethyl-2-(1-{3-[(tert.-butoxycarbonyl)amino]propyl}-1H-indol-3-yl)-2-oxoacetate (5.3 mmol, 74%) as pale yellow crystals. Mp 89-90° C. IR ṽ [cm$^{-1}$]=3392; 2977; 2936; 1727; 1698; 1619; 1515. EI-MS m/z (rel. int.)=374 (8.9%; M$^{+\cdot}$). $^1$H NMR (300 MHz, CDCl$_3$) 8.45 (m; 2H; indole-H); 7.35 (m; 3H; indole-H); 4.63 (bs; 1H; NH); 4.41 (q; $^3$J=7.1 Hz; 2H; OC$\underline{H}_2$CH$_3$); 4.24 (t; $^3$J=7.1 Hz; 2H; indole-CH$_2$); 3.18 (q; $^3$J=6.1 Hz; 2H; CH$_2$N); 2.09 (m; 2H; CH$_2$C$\underline{H}_2$CH$_2$); 1.44 (s; 9H; C(CH$_3$)$_3$); 1.43 (t; $^3$J=7.1 Hz; 3H; OCH$_2$C$\underline{H}_3$).

The general procedure 2 was then followed using ethyl-2-(1-{3-[(tert.-butoxycarbonyl)amino]propyl}-1H-indol-3-yl)-2-oxoacetate (6.8 mmol, 2.5 g), 3,4,5-trimethoxyphenylacetamide (6.8 mmol, 1.5 g) and 1 M tert.-BuOK (14.4 mmol, 14.4 ml). The purification was achieved by column chromatography (petrolether:ethylacetate 1:1) to yield 3-(1-{3-[(tert.-butoxycarbonyl)amino]propyl}-1H-indol-3-yl)-4-(3,4,5-trimethoxyphenyl)-maleinimide (2.5 mmol, 36.8%) as orange crystals. Mp 178-179° C. IR ṽ [cm$^{-1}$]=3408; 1714; 1689; 1613; 1515. FD-MS m/z (rel. int.)=535.5 (100%). $^1$H NMR (300 MHz, CDCl$_3$) 7.95 (s; 1H; indole-H); 7.60 (bs; 1H; imide-NH); 7.32 (d; $^3$J=8.2 Hz; 1H; indole-H); 7.16 (t; $^3$J=7.2 Hz; 1H; indole-H); 6.85 (t; $^3$J=7.2 Hz; 1H; indole-H); 6.79 (s; 2H; 2×Ar—H); 6.47 (d; $^3$J=8.2 Hz; 1H; indole-H); 4.65 (bs; 1H; NH); 4.26 (t; $^3$J=7.10 Hz; 2H; indole-CH$_2$); 3.85 (s; 3H; OCH$_3$); 3.49 (s; 6H; 2×OCH$_3$); 3.16 (m; 2H; CH$_2$N); 2.11 (m; 2H; CH$_2$C$\underline{H}_2$CH$_2$); 1.44 (s; 9H; C(CH$_3$)$_3$).

A stirred solution of 3-(1-{3-[(tert.-butoxycarbonyl)amino]propyl}-1H-indol-3-yl)-4-(3,4,5-trimethoxyphenyl)-maleinimide (2.5 mmol, 1.32 g) in 150 ml ethanol and 2.3 M ethanolic HCl (11.25 mmol, 4.9 ml) was heated to 80° C. for 3 hours. The precipitate was filtered and washed with ethanol to give the title compound (2.2 mmol, 88%) as orange crystals. Mp 274-275° C. IR ṽ [cm$^{-1}$]=3145; 2958; 1761; 1708; 1597; 1499. EI-MS m/z (rel. int.)=438 (5.6%; M$^{+\cdot}$). $^1$H NMR (300 MHz, CDCl$_3$) 11.11 (s; 1H; imide-NH); 8.07 (s; 1H;

indole-H); 7.96 (bs; 3H; NH$_3$); 7.62 (d; $^3$J=8.1 Hz; 1H; indole-H); 7.16 (t; $^3$J=7.7 Hz; 1H; indole-H); 6.80 (t; $^3$J=7.7 Hz; 1H; indole-H); 6.72 (s; 2H; 2×Ar—H); 6.36 (d; $^3$J=8.1 Hz; 1H; indole-H); 4.42 (t; $^3$J=6.7 Hz; 2H; indole-CH$_2$); 3.65 (s; 3H; OCH$_3$); 3.36 (s; 6H; 2×OCH$_3$); 2.75 (dd; 2H; $^3$J=6.7 Hz; $^3$J=12.3 Hz; CH$_2$N); 2.07 (m; 2H; CH$_2$CH$_2$CH$_2$). Anal. calcd for C$_{24}$H$_{26}$ClN$_3$O$_5$: C, 61.08; H, 5.55; N, 8.90. Found: C, 60.96; H, 5.35; N, 8.88.

Example H 3-(1-[2-Hydroxyethyl]-1H-indol-3-yl)-4-(3,4,5-trimethoxyphenyl)-maleinimide

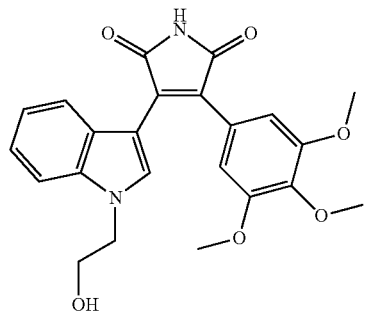 [SMILES: COc1cc(C2=C(c3cn(CCO)c4ccccc34)C(=O)NC2=O)cc(OC)c1OC]

A modified procedure of Galka et al., *J. Lab. Comp. Rad.* 2005, 48, 11, 797-809, was used. A mixture of 2-bromoethanol (6.6 mmol; 0.83 g=0.47 ml), tert.-butyldimethylsilylchloride (6.6 mmol, 1.0 g) and imidazole (7.3 mmol; 0.5 g) was stirred at RT for 3 hours under nitrogen atmosphere. The reaction was quenched with water, extracted with diethylether. The organic phases were dried over Na$_2$SO$_4$, filtered and concentrated. The purification was achieved by column chromatography (petrolether) to yield 2-bromoethoxy)(tert.-butyl)dimethylsilane (6.4 mmol, 96%). $^1$H NMR (300 MHz, CDCl$_3$) 3.91 (t; $^3$J=6.5 Hz; 2H; OCH$_2$); 3.41 (t; $^3$J=6.5 Hz; 2H; CH$_2$Br); 0.93 (s; 9H; C(CH$_3$)$_3$); 0.11 (s; 6H; 2×CH$_3$).

The general procedure 1 was then followed using the above product (6.4 mmol, 1.53 g), ethyl-2-(1H-indol-3-yl)-2-oxoacetate (5.99 mmol, 1.3 g) and Cs$_2$CO$_3$ (8.1 mmol, 2.63 g). The purification was achieved by column chromatography (petrol-ether:ethylacetate 7:3) to yield ethyl-2-(1-{2-[{1-(tert.-butyl)-1,1-dimethylsilyl}oxy]-ethyl}-1H-indol-3-yl)-2-oxoacetate (4.37 mmol, 73%) as pale yellow oil. IR $\tilde{\nu}$ [cm$^{-1}$]=2958; 2923; 2857; 1736; 1635; 1514; 1461. EI-MS m/z (rel. int.)=375 (6.0%; M$^{+\cdot}$). $^1$H NMR (300 MHz, CDCl$_3$) 8.45 (m; 1H; indole-H); 8.42 (s; 1H; indole-H); 7.37 (m; 3H; indole-H); 4.41 (q; $^3$J=7.1 Hz; 2H; OCH$_2$CH$_3$); 4.29 (t; $^3$J=5.1 Hz; 2H; indole-CH$_2$CH$_2$O); 3.95 (t; $^3$J=5.1 Hz; 2H indole-CH$_2$CHO); 1.43 (t; $^3$J=7.1 Hz; 3H; OCH$_2$CH$_3$); 0.80 (s; 9H; C(CH$_3$)$_3$); −0.17 (s; 6H; 2×CH$_3$).

The general procedure 2 was then followed using ethyl-2-(1-{2-[{1-(tert.-butyl)-1,1-dimethylsilyl}oxy]ethyl}-1H-indol-3-yl)-2-oxoacetate (1.8 mmol, 0.69 g), 3,4,5-trimethoxyphenylacetamide (1.6 mmol, 0.36 g) and 1 M tert.-BuOK (6 mmol, 6 ml). The purification was achieved by column chromatography (petrolether:ethylacetate 7:3) to yield 3-(1-{2-[{1-(tert.-butyl)-1,1-dimethylsilyl}oxy]ethyl}-1H-indol-3-yl)-4-(3,4,5-trimethoxyphenyl)-maleinimide (0.7 mmol, 39%) as an orange oil. IR $\tilde{\nu}$ [cm$^{-1}$]=3186; 2980; 2930; 2879; 1692. EI-MS m/z (rel. int.)=536 (68%; M$^{+\cdot}$). $^1$H NMR (300 MHz, CDCl$_3$) 8.06 (s; 1H; indole-H); 7.34 (d; $^3$J=8.1 Hz; 2H; indole-H); 7.29 (bs, 1H; imide-NH) 7.15 (t; $^3$J=7.5 Hz; 1H; indole-H); 6.84 (t; $^3$J=7.5 Hz; 1H; indole-H); 6.77 (s; 2H; Ar—H); 6.42 (d; $^3$J=8.1 Hz; 1H; indole-H); 4.31 (t; $^3$J=5.2 Hz; 2H; indole-CH$_2$CH$_2$O); 3.98 (t; $^3$J=5.2 Hz; 2H indole-CH$_2$CH$_2$O); 3.86 (s; 3H; OCH$_3$); 3.50 (s; 6H; 2×OCH$_3$); 0.82 (s; 9H; C(CH$_3$)$_3$); −0.13 (s; 6H; Si(CH$_3$)$_2$).

A modified procedure of Csuk et al., *Z. Naturforsch.*, 2003, 58b, 97-105, was used. Tetrabutylammoniumfluoride (0.79 mmol, 0.25 g) was added to a stirred solution of the above product (0.7 mmol, 0.26 g) in 10 ml THF (tetrahydrofurane). After the reaction was completed (TLC-control) (TLC=thin layer chromatography) it was concentrated. The purification was achieved by column chromatography (petrol-ether:ethylacetate:methanol 2:7:1) to yield 3-(1-[2-hydroxyethyl]-1H-indol-3-yl)-4-(3,4,5-trimethoxyphenyl)-maleinimide (0.4 mmol, 58%) as dark red crystals. Mp=195-196° C. IR $\tilde{\nu}$ [cm$^{-1}$]=3221; 1746; 1705. EI-MS m/z (rel. int.)=422 (100%; M$^{+\cdot}$). $^1$H NMR (300 MHz, CDCl$_3$) 8.02 (s; 1H; indole-H); 7.37 (d; $^3$J=7.9 Hz; 1H; indole-H); 7.32 (s; 1H; imide-NH); 7.17 (t; $^3$J=7.7 Hz; 1H; indole-H); 6.87 (t; $^3$J=7.7 Hz; 1H; indole-H); 6.79 (s; 2H; Ar—H); 6.50 (d; $^3$J=7.9 Hz; 1H; indole-H); 4.37 (t; $^3$J=5.2 Hz; 2H; indole-CH$_2$); 4.06 (q; $^3$J=5.0 Hz; 2H; CH$_2$O); 3.86 (s; 3H; OCH$_3$); 3.50 (s; 6H; 2×OCH$_3$). Anal. calcd for C$_{23}$H$_{22}$N$_2$O$_6$: C, 65.39; H, 5.25; N, 6.63. Found: C, 65.35; H, 5.33; N, 6.70.

Example I 3-(1-[3-Hydroxypropyl]-1H-indol-3-yl)-4-(3,4,5-trimethoxyphenyl)-maleinimide

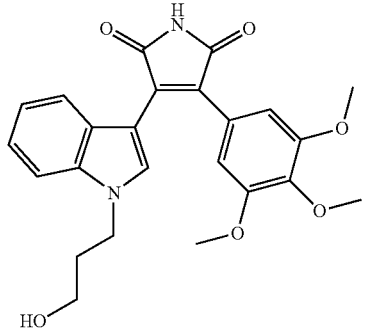 [SMILES: COc1cc(C2=C(c3cn(CCCO)c4ccccc34)C(=O)NC2=O)cc(OC)c1OC]

(3-Bromopropoxy)-tert.-butyldimethylsilane (36.4 mmol, 93%) was synthesized using the same procedure as for example 3. $^1$H NMR (300 MHz, CDCl$_3$) 3.73 (t; $^3$J=5.7 Hz; 2H; CH$_2$O); 3.51 (t; $^3$J=6.4 Hz; 2H; CH$_2$Br); 2.02 (q; $^3$J=5.7 Hz; $^3$J=6.4 Hz; 2H; CH$_2$CH$_2$CH$_2$); 0.89 (s; 9H; C(CH$_3$)$_3$); 0.06 (s; 6H; 2×CH$_3$).

The general procedure 1 was then followed using the above product (7.9 mmol, 2 g), ethyl-2-(1H-indol-3-yl)-2-oxoacetate (7.4 mmol, 1.61 g) and Cs$_2$CO$_3$ (10 mmol, 3.25 g). The purification was achieved by column chromatography (petrol-ether:ethylacetate 9:1) to yield ethyl-2-(1-{3-[{1-(tert.-butyl)-1,1-dimethylsilyl}oxy]-propyl}-1H-indol-3-yl)-2-oxoacetate (6.7 mmol, 91%) as pale yellow crystals. Mp=51-52° C. IR $\tilde{\nu}$ [cm$^{-1}$]=3142; 2958; 2924; 2867; 1727; 1638. EI-MS m/z (rel. int.)=389 (5.2%; M$^{+\cdot}$). $^1$H NMR (300 MHz, CDCl$_3$) 8.46 (m; 1H; indole-H); 8.37 (s; 1H; indole-H); 7.43 (m; 1H; indole-H); 7.34 (m; 2H; indole-H); 4.41 (q; $^3$J=7.1 Hz; 2H; OCH$_2$CH$_3$); 4.33 (t; $^3$J=6.8 Hz; 2H; indole-CH$_2$); 3.58 (t; $^3$J=5.5 Hz; 2H; CH$_2$O); 2.06 (m; 2H; indole-CH$_2$CH$_2$O); 1.43 (t; J=7.1 Hz; 3HOCH$_2$CH$_3$); 0.94 (s; 9H); 0.07 (s; 6H).

The general procedure 2 was then followed using ethyl-2-(1-{3-[{1-(tert.-butyl)-1,1-dimethylsilyl}oxy]propyl}-1H-indol-3-yl)-2-oxoacetate (6.7 mmol, 2.64 g), 3,4,5-trimethoxyphenylacetamide (6.04 mmol, 1.36 g) and 1 M tert.-BuOK (18 mmol, 18 ml). The purification was achieved by column chromatography (petrol-ether:ethylacetate 7:3) to yield 3-(1-{3-[{1-(tert.-butyl)-1,1-dimethylsilyl}oxy]propyl}-1H-indol-3-yl)-4-(3,4,5-trimethoxyphenyl)-maleinimide (3 mmol, 45%) as yellow crystals. Mp=99-100° C. IR $\tilde{\nu}$ [cm$^{-1}$]=3202; 3066; 2955; 2923; 2854; 1771; 1701. EI-MS m/z (rel. int.)=551 (86.49%; M$^{+\bullet}$). $^1$H NMR (300 MHz, CDCl$_3$) 8.30 (bs; 1H; imide-NH); 7.98 (s; 1H; indole-H); 7.38 (d; $^3$J=8.1 Hz; 1H; indole-H); 7.15 (t; $^3$J=7.6 Hz; 1H; indole-H); 6.85 (t; $^3$J=7.6 Hz; 1H; indole-H); 6.80 (s; 2H; Ar—H); 6.47 (d; $^3$J=8.1 Hz; 1H; indole-H); 4.34 (t; $^3$J=6.8 Hz; 2H; indole-CH$_2$CH$_2$CH$_2$O); 3.86 (s; 3H; OCH$_3$); 3.60 (t; $^3$J=5.5 Hz; 2H indole-CH$_2$CH$_2$CH$_2$O); 3.49 (s; 6H; 2×OCH$_3$); 2.08 (m; 2H; indole-CH$_2$CH$_2$CH$_2$O); 0.94 (s; 9H; SiC(CH$_3$)$_3$); 0.07 (s; 6H; Si(CH$_3$)$_2$).

3-(1-[3-Hydroxypropyl]-1H-indol-3-yl)-4-(3,4,5-trimethoxyphenyl)-maleinimide (2.25 mmol, 75%) was synthesized using the same procedure as for example 3. Mp=160° C. IR $\tilde{\nu}$ [cm$^{-1}$]=3367; 2980; 2882; 1708. EI-MS m/z (rel. int.)=437 (100%; M$^{+\bullet}$). $^1$H NMR (300 MHz, CDCl$_3$) 7.97 (s; 1H; indole-NH); 7.38 (m; 2H; indole-H+imide-NH); 7.17 (t; $^3$J=7.6 Hz; 1H; indole-H); 6.86 (t; $^3$J=7.6 Hz; 1H; indole-H); 6.79 (s; 2H; Ar—H); 6.49 (d; $^3$J=8.1 Hz; 1H; indole-H); 4.39 (t; $^3$J=6.79 Hz; 2H; indole-CH$_2$CH$_2$CH$_2$O); 3.86 (s; 3H; OCH$_3$); 3.65 (t; $^3$J=5.67 Hz; 2H; indole-CH$_2$CH$_2$CH$_2$O); 3.50 (s; 6H; 2×OCH$_3$); 2.13 (m, 2H; indole-CH$_2$CH$_2$CH$_2$O). Anal. calcd for C$_{24}$H$_{24}$N$_2$O$_6$: C, 66.04; H, 5.54; N, 6.42. Found: C, 65.93; H, 5.63; N, 6.34.

Example J

3-{1-[2-(Dimethylamino)ethyl]-1H-indol-3-yl}-4-(3,4,5-trimethoxyphenyl)-maleinimide

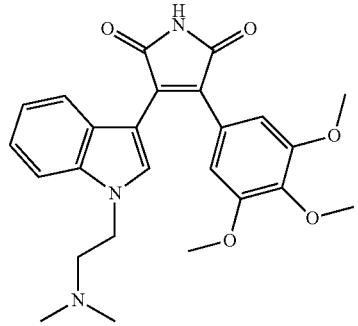 [SMILES: COc1cc(C2=C(c3cn(CCN(C)C)c4ccccc34)C(=O)NC2=O)cc(OC)c1OC]

The general procedure 1 was then followed using 1-chloro-2-dimethylaminoethane (6 mmol, 0.65 g), ethyl-2-(1H-indol-3-yl)-2-oxoacetate (6 mmol, 1.3 g) and Cs$_2$CO$_3$ (6.6 mmol, 2.15 g). The purification was achieved by column chromatography (petrolether:ethylacetate:diethylamine 6:3:1) to yield ethyl-2-{1-[2-(dimethylamino)-ethyl]-1H-indol-3-yl}-2-oxoacetate (3.7 mmol, 62%) as pale yellow crystals. Mp=71-72° C. IR $\tilde{\nu}$ [cm$^{-1}$]=3139; 3044; 2977; 2946; 2797; 2772; 1727; 1641. EI-MS m/z (rel. int.)=288 (19.15%; M$^{+\bullet}$). $^1$H NMR (300 MHz, CDCl$_3$) 8.45 (m; 2H; indole-H); 7.37 (m; 3H; indole-H); 4.41 (q; $^3$J=7.1 Hz; 2H; OCH$_2$CH$_3$); 4.26 (t; $^3$J=6.9 Hz; 2H; indole-CH$_2$CH$_2$N); 2.76 (t; $^3$J=6.9 Hz; 2H; indole-CH$_2$CH$_2$N); 2.31 (s; 6H); 1.44 (t; 3H; $^3$J=7.1 Hz; OCH$_2$CH$_3$).

The general procedure 2 was then followed using the above product (3.7 mmol, 1.07 g), 3,4,5-trimethoxyphenylacetamide (3.7 mmol, 0.83 g) and 1 M tert.-BuOK (10 mmol, 10 ml). The purification was achieved by column chromatography (dichloromethane:methanol 9:1) to yield 3-{1-[2-(dimethylamino)ethyl]-1H-indol-3-yl}-4-(3,4,5-trimethoxyphenyl)-maleinimide (1.34 mmol, 36%) as yellow crystals. Mp=184-185° C. IR $\tilde{\nu}$ [cm$^{-1}$]=2980; 2920; 1701. EI-MS m/z (rel. int.)=449 (100%; M$^{+\bullet}$). $^1$H NMR (300 MHz, CDCl$_3$) 8.04 (s; 1H; indole-H); 7.97 (bs; 1H; NH); 7.34 (d; $^3$J=8.2 Hz; 1H; indole-H); 7.16 (t; $^3$J=7.6 Hz; 1H; indole-H); 6.85 (t; $^3$J=7.6 Hz; 1H; indole-H); 6.75 (s; 2H; Ar—H); 6.45 (d; $^3$J=8.2 Hz; 1H; indole-H); 4.32 (t; $^3$J=6.8 Hz; 2H indole-CH$_2$CH$_2$N); 3.84 (s; 3H; OCH$_3$); 3.47 (s; 6H; 2×OCH$_3$); 2.80 (t; $^3$J=6.8 Hz; 2H, indole-CH$_2$CH$_2$N); 2.32 (s; 6H; N(CH$_3$)$_2$). Anal. calcd for C$_{25}$H$_{27}$N$_3$O$_5$: C, 66.8; H, 6.05; N, 9.35. Found: C, 66.91; H, 6.05; N, 9.29.

Example K

3-{1-[3-(Dimethylamino)propyl]-1H-indol-3-yl}-4-(3,4,5-trimethoxyphenyl) maleinimide

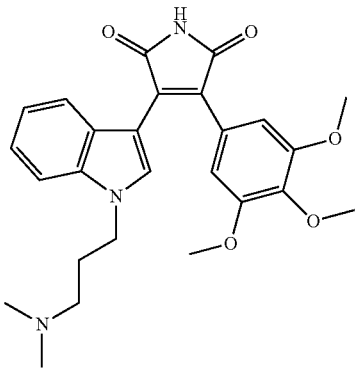

The general procedure 1 was then followed using 1-chloro-3-dimethylaminopropane (7 mmol, 0.75 g), ethyl-2-(1H-indol-3-yl)-2-oxoacetate (6 mmol, 1.3 g) and Cs$_2$CO$_3$ (6.6 mmol, 2.15 g). The purification was achieved by column chromatography (petrolether:ethylacetate:diethylamine 6:3:1) to yield ethyl-2-{1-[2-(dimethylamino)ethyl]-1H-indol-3-yl}-2-oxoacetate (3.8 mmol, 63%) as an pale yellow oil. IR $\tilde{\nu}$ [cm$^{-1}$]=3023; 2962; 2917; 1732; 1630. EI-MS m/z (rel. int.)=302 (8.21%; M$^{+\bullet}$). $^1$H NMR (300 MHz, CDCl$_3$) 8.43 (m; 1H; indole-H); 8.39 (s; 1H; indole-H); 7.33 (m; 3H; indole-H); 4.40 (q; $^3$J=7.1 Hz; 2H; OCH$_2$CH$_3$); 4.27 (t; $^3$J=6.8 Hz; 2H; indole-CH$_2$CH$_2$CH$_2$N); 2.22 (s; 6H; N(CH$_3$)$_2$); 2.20 (m; 2H; indole-CH$_2$CH$_2$CH$_2$N); 2.00 (quint; $^3$J=6.7 Hz; 2H; indole-CH$_2$CH$_2$CH$_2$N); 1.42 (t; $^3$J=7.1 Hz; 3HOCH$_2$CH$_3$).

The general procedure 2 was then followed using the above product (3.8 mmol, 1.15 g), 3,4,5-trimethoxyphenylacetamide (3.8 mmol, 0.83 g) and 1 M tert.-BuOK (10 mmol, 10 ml). The purification was achieved by column chromatography (dichloromethane:methanol 8:2) to yield 3-{1-[3-(dimethylamino)propyl]-1H-indol-3-yl}-4-(3,4,5-trimethoxyphenyl)-maleinimide (0.73 mmol, 19%) as orange crystals. Mp=187-188° C. IR $\tilde{\nu}$ [cm$^{-1}$]=2939; 1705; 1613; 1578. EI-MS m/z (rel. int.)=463 (36.77%; M$^{+\bullet}$). $^1$H NMR (300 MHz, CDCl$_3$) 8.01 (s; 1H; indole-H); 7.78 (bs; 1H; imide-NH); 7.37 (d; $^3$J=8.1 Hz; 1H; indole-H); 7.16 (t; $^3$J=7.6 Hz; 1H; indole-H); 6.85 (t; $^3$J=7.6 Hz; 1H; indole-H); 6.79 (s; 2H; Ar—H);

6.46 (d; ³J=8.1 Hz; 1H; indole-H); 4.31 (t; ³J=6.8 Hz; 2H; indole-C<u>H</u>₂CH₂CH₂N); 3.85 (s; 3H; OCH₃); 3.49 (s; 6H; 2×OCH₃); 2.28 (m; 8H; indole-CH₂CH₂C<u>H</u>₂N+N(CH₃)₂); 2.06 (m; 2H; indole-C<u>H</u>₂CH₂N). Anal. calcd for C₂₆H₂₉N₃O₅ (×⅔H₂O) C, 65.67; H, 6.43; N, 8.84. Found: C, 65.46; H, 6.13; N, 8.62.

Example L

3-{1-[2-(piperidin-1-yl)ethyl]-1H-indol-3-yl}-4-(3,4,5-trimethoxyphenyl)-maleinimide

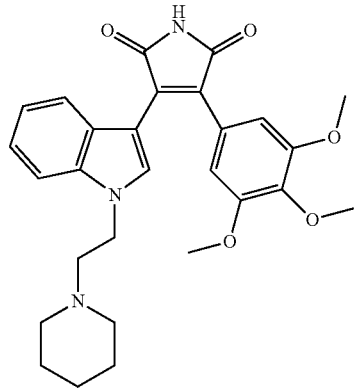 [SMILES: COc1cc(C2=C(c3cn(CCN4CCCCC4)c4ccccc34)C(=O)NC2=O)cc(OC)c1OC]

The general procedure 1 was then followed using 1-(2-chloroethyl)piperidine (10 mmol, 1.5 g), ethyl-2-(1H-indol-3-yl)-2-oxoacetate (7 mmol, 1.5 g) and K₂CO₃ (10.9 mmol, 1.5 g). The purification was achieved by column chromatography (petrol-ether:ethylacetate:diethylamine 8:1:1) to yield ethyl-2-{1-[2-(piperidin-1-yl)ethyl]-1H-indol-3-yl}2-oxoacetate (4.6 mmol, 66%) as an pale yellow oil. IR ν̃ [cm⁻¹]=2936; 2857; 1730; 1638. EI-MS m/z (rel. int.)=328 (18.99%; M⁺•). ¹H NMR (300 MHz, CDCl₃) 8.43 (m; 2H; indole-H); 7.35 (m; 3H; indole-H); 4.40 (q; ³J=7.1 Hz; 2H; OC<u>H</u>₂CH₃); 4.25 (t; ³J=6.8 Hz; 2H; indole-C<u>H</u>₂CH₂N); 2.72 (t; ³J=6.8 Hz; 2H; indole-CH₂C<u>H</u>₂N); 2.43 (m; 4H; piperidin-CH₂ (C-2+6)); 1.57 (m; 4H; piperidin-CH₂ (C-3+5)); 1.43 (m; 5H; piperidin-CH₂ (C-4)+OCH₂C<u>H</u>₃).

The general procedure 2 was then followed using the above product (4.6 mmol, 1.51 g), 3,4,5-trimethoxyphenylacetamide (4.6 mmol, 1.04 g) and 1 M tert.-BuOK (14 mmol, 14 ml). The purification was achieved by column chromatography (dichloromethane:methanol 9:1) to yield 3-{1-[2-(piperidin-1-yl)ethyl]-1H-indol-3-yl}-4-(3,4,5-trimethoxyphenyl)-maleinimide (1.6 mmol, 35%) as yellow crystals. Mp=179-180° C. IR ν̃ [cm⁻¹]=3132; 2939; 2829; 1704; 1629. EI-MS m/z (rel. int.)=491 (31.97%; M⁺•). ¹H NMR (300 MHz, CDCl₃) 8.18 (bs; 1H; imide-NH); 8.12 (s; 1H; indole-H); 7.35 (d; ³J=8.1 Hz; 1H; indole-H); 7.16 (t; ³J=7.6 Hz; 1H; indole-H); 6.85 (t; ³J=7.6 Hz; 1H; indole-H); 6.77 (s; 2H; Ar—H); 6.44 (d; ³J=8.1 Hz; 1H; indole-H); 4.34 (t; ³J=7.0 Hz; 2H; indole-C<u>H</u>₂CH₂N); 3.85 (s; 3H; OCH₃); 3.48 (s; 6H; 2×OCH₃); 2.80 (t; ³J=7.0 Hz; 2H; indole-CH₂C<u>H</u>₂N); 2.49 (m; 4H; piperidin-CH₂ (C-2+6)); 1.62 (m; 4H; piperidin-CH₂ (C-3+5)); 1.46 (m; 2H; piperidin-CH₂ (C4)). Anal. calcd for C₂₈H₃₁N₃O₅ (×H₂O) C, 66.26; H, 6.55; N, 8.28. Found: C, 66.50; H, 6.57; N, 7.83.

Example M

3-{1-(2-morpholinoethyl)-1H-indol-3-yl}-4-(3,4,5-trimethoxyphenyl)-maleinimide

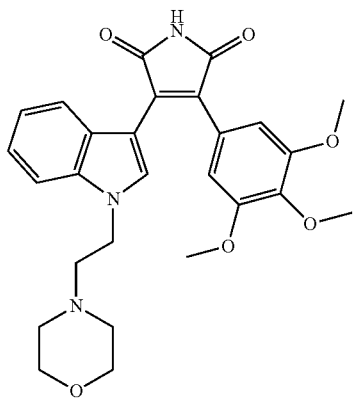 [SMILES: COc1cc(C2=C(c3cn(CCN4CCOCC4)c4ccccc34)C(=O)NC2=O)cc(OC)c1OC]

The general procedure 1 was then followed using 1-(2-chloroethyl)morpholine (10 mmol, 1.5 g), ethyl-2-(1H-indol-3-yl)-2-oxoacetate (7 mmol, 1.5 g) and K₂CO₃ (10.9 mmol, 1.5 g). The purification was achieved by column chromatography (petrolether:ethylacetate:diethylamine 5:5:1) to yield ethyl-2-[1-(2-morpholinoethyl)-1H-indol-3-yl]-2-oxoacetate (3.8 mmol, 55%) as pale yellow crystals. Mp 99-100° C. IR ν̃ [cm⁻¹]=3164; 2955; 2822; 1717; 1625. EI-MS m/z (rel. int.)=330 (19.60%; M⁺•). ¹H NMR (300 MHz, CDCl₃) 8.45 (m; 2H; indole-H); 7.37 (m; 3H; indole-H); 4.41 (q; ³J=7.1 Hz; 2H; OC<u>H</u>₂CH₃); 4.27 (t; ³J=6.5 Hz; 2H; indole-C<u>H</u>₂CH₂N); 3.71 (m; 4H; morpholin-CH₂ (C3+5)); 2.79 (t; 2H; ³J=6.5 Hz; indole-CH₂C<u>H</u>₂N); 2.49 (m; 4H; morpholin-CH₂(C2+6)); 1.44 (t; J=7.1 Hz; 3H; OCH₂C<u>H</u>₃).

The general procedure 2 was then followed using the above product (3.8 mmol, 1.25 g), 3,4,5-trimethoxyphenylacetamide (3.8 mmol, 0.85 g) and 1 M tert.-BuOK (12 mmol, 12 ml). The purification was achieved by column chromatography (dichloromethane:methanol 9:1) to yield 3-{1-(2-morpholinoethyl)-1H-indol-3-yl}-4-(3,4,5-trimethoxyphenyl)-maleinimide (1 mmol, 27%) as orange crystals. Mp=238-239° C. IR ν̃ [cm⁻¹]=3145; 2955; 1857; 1698; 1616. EI-MS m/z (rel. int.)=492 (44.94%; M⁺•). ¹H NMR (300 MHz, DMSO) 11.04 (bs; 1H; imide-NH); 8.07 (s; 1H; indole-H); 7.56 (d; ³J=8.1 Hz; 1H; indole-H); 7.13 (t; ³J=7.6 Hz; 1H; indole-H); 6.78 (t; ³J=7.6 Hz; 1H; indole-H); 6.72 (s; 2H; Ar—H); 6.36 (d; ³J=8.1 Hz; 1H; indole-H); 4.40 (t; ³J=6.0 Hz; 2H; indole-C<u>H</u>₂CH₂N); 3.66 (s; 3H; OCH₃); 3.52 (m; 4H; morpholin-CH₂(C3+5)); 3.37 (s; 6H; 2×OCH₃); 2.68 (t; ³J=6.0 Hz; 2H; indole-CH₂C<u>H</u>₂N); 2.40 (m; 4H; morpholin- CH₂ (C2+6)). Anal. calcd for $C_{27}H_{29}N_3O_6$ (×½$H_2O$) C, 64.79; H, 6.04; N, 8.39. Found: C, 64.63; H, 6.03; N, 8.23.

Example N

3-{1-[3-(4-Methylhexahydro-1-pyrazindiiumyl)propyl]-1H-indol-3-yl}-4-(3,4,5-trimethoxyphenyl)-maleinimide dichloride

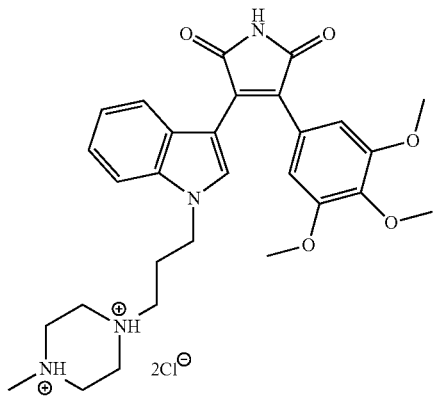

A modified procedure of Mahesh et al., *Pharmazie*, 2005, 60, 6, 411-414, was used. After cooling a stirred solution of N-methylpiperazine (50 mmol, 5.55 ml) in 100 ml acetone to 0° C., 10 ml of an aqueous 25% NaOH-solution and 1-bromo-3-chloropropane (50 mmol, 7.87 g=4.92 ml) were added cautiously. The reaction was stirred at RT for 24 hours. After concentrating the mixture under reduced pressure, the residue was diluted with water and extracted with dichloromethane. The collected organic phases were dried over $Na_2SO_4$, filtered and concentrated. The residue was diluted with ethanol and after adding 2.3 M ethanolic HCl 1-(3-chloropropyl)-4-methylpiperazin-dihydrochloride crystallized as white crystals (12.5 mmol, 25%). Mp=257° C. ¹H NMR (300 MHz, DMSO) 3.74 (t; 2H; ³J=6.4 Hz; NCH₂CH₂CH₂Cl); 3.37 (m; 12H; NCH₂CH₂CH₂Cl+4×piperazin-CH₂+2×NH); 2.81 (s; 3H; CH₃); 2.19 (d; 2H; ³J=6.8 Hz; NCH₂CH₂CH₂Cl).

The general procedure 1 was then followed using 1-(3-chloropropyl)-4-methylpiperazine (12.5 mmol, 2.2 g), ethyl-2-(1H-indol-3-yl)-2-oxoacetate (10 mmol, 2.17 g) and $K_2CO_3$ (10.8 mmol, 1.5 g). The purification was achieved by column chromatography (petrolether:ethylacetate:diethylamine 5:5:1) to yield ethyl-2-{1-[3-(4-methylpiperazin-1-yl)propyl]-1H-indol-3-yl}-2-oxoacetate (5.3 mmol, 42%). IR ṽ [cm⁻¹]=2936; 2790; 1727; 1638. FD-MS m/z (rel. int.) =359.9 (2.05%; M⁺ᐧ). ¹H NMR (300 MHz, CDCl₃) 8.40 (m; 2H; indole-H); 7.36 (m; 3H; indole-H); 4.38 (q; ³J=7.1 Hz; 2H; OCH₂CH₃); 4.25 (t; ³J=6.5 Hz; 2H; indole-CH₂CH₂CH₂N); 2.44 (m; 8H; 4'piperazin-CH₂); 2.30 (s; 3H; CH₃); 2.26 (t; ³J=6.5 Hz; 2H; indole-CH₂CH₂CH₂N); 2.00 (m; 2H;

The general procedure 2 was then followed using the above product (5.3 mmol, 1.9 g), 3,4,5-trimethoxyphenylacetamide (5.3 mmol, 1.2 g) and 1 M tert.-BuOK (15 mmol, 15 ml). The purification was achieved by column chromatography (dichloromethane:methanol 8:2). The product was diluted with ethanol and after adding 2.3 M ethanolic HCl 3-{1-[3-(4-methylhexahydro-1-pyrazindiiumyl)propyl]-1H-indol-3-yl}-4-(3,4,5-trimethoxyphenyl)-maleinimide dichloride crystallized as orange crystals (0.93 mmol, 29%). Mp=225-226° C. IR ṽ [cm⁻¹]=3088; 2996; 2958; 1695. EI-MS m/z (rel. int.)=520 (27.12%; M⁺ᐧ). ¹H NMR (300 MHz, DMSO) 11.11 (bs; 1H; imide-NH); 8.09 (s; 1H; indole-H); 7.64 (d; ³J=8.1 Hz; 1H; indole-H); 7.15 (t; ³J=7.6 Hz; 1H; indole-H); 6.80 (t; ³J=7.6 Hz; 1H; indole-H); 6.73 (s; 2H; Ar—H); 6.35 (d; ³J=8.1 Hz; 1H; indole-H); 4.43 (m; 2H; indole-CH₂CH₂CH₂N); 3.70 (m; 12H; 4×piperazin-CH₂+2×NH+indole-CH₂CH₂CH₂N); 3.65 (s; 3H; OCH₃); 3.37 (s; 6H; 2×OCH₃); 2.80 (s; 3H; CH₃); 2.24 (m; 2H; indole-CH₂CH₂CH₂N). Anal. calcd for $C_{29}H_{36}Cl_2N_4O_5$ (×2HCl×$H_2O$) C, 57.14; H, 6.28; N, 9.19. Found: C, 57.10; H, 6.30; N, 8.68.

Example O 3-(5-Fluoro-1H-indol-3-yl)-4-(3,4,5-trimethoxyphenyl)-maleinimide

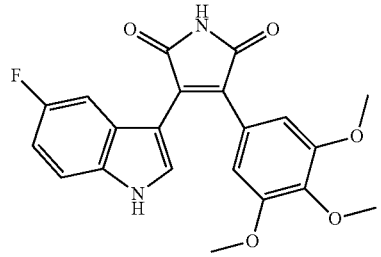 [SMILES: COc1cc(C2=C(c3c[nH]c4ccc(F)cc34)C(=O)NC2=O)cc(OC)c1OC]

A modified procedure of Catarzi et al., *Arch. Pharm.* (*Weinheim*) 1997, 330, 12, 383-386, was used to prepare ethyl 2-(5-fluoro-1H-indol-3-yl)-2-oxoacetate. A stirred solution of 5-fluoroindole (7.4 mmol, 1.0 g) and pyridine (0.8 ml) in 30 ml diethylether was cooled to 0° C. Ethyloxalylchloride (8.9 mmol; 1.21 g=1.5 ml) was added cautiously over a period of 20 min. The reaction was stirred for 1 h at a temperature of 0° C. and afterwards 4 h at room temperature. The precipitate was filtered, washed with cold diethylether and water to give ethyl 2-(5-fluor-1H-indol-3-yl)-2-oxoacetate (8 mmol; 64.8%) as pale yellow crystals. The collected organic phase was dried over $Na_2SO_4$, filtered, concentrated and purified by column chromatography (petrolether:ethylacetate 1:1). IR ṽ [cm⁻¹]=3158; 2978; 1724; 1614. EI-MS m/z (rel. Int.)=235 (9.64%; M⁺ᐧ). ¹H NMR (300 MHz, CDCl₃) 9.22 (bs, 1H; NH); 8.53 (d; J=3.3 Hz; 1H; indole-H); 8.11 (dd; J=2.5 Hz; J=9.0 Hz; 1H; indole-H); 7.41 (dd; J=4.3 Hz; J=9.0 Hz; 1H; indole-H); 7.06 (dt; J=2.5 Hz; J=9.0 Hz; 1H; indole-H); 4.41 (q; ³J=7.1 Hz; 2H; OCH₂CH₃); 1.43 (t; ³J=7.1 Hz; 3H; OCH₂CH₃).

A modified procedure of Basel et al., *J. Org. Chem.*, 2000, 65, 20, 6368-6380, was used to prepare ethyl-2-[1-(tert.-butoxycarbonyl)-5-fluoro-1H-indol-3-yl]-2-oxoacetate. To a stirred suspension of the above ethyl 2-(5-fluoro-1H-indol-3-yl)-2-oxoacetate (4.8 mmol; 1.1 g) and di-tert.-butyldicarbonat (4.8 mmol; 1.05 g) in 30 ml dichloromethan a catalytic amounts of DMAP (dimethylaminopyridine) was added. The suspension becomes a clear solution of adding DMAP. The reaction was stirred over night, concentrated and purified by column chromatography (dichloromethane) to obtain ethyl-2-[1-(tert.-butoxycarbonyl)-5-fluoro-1H-indol-3-yl]-2-oxoacetate as white crystals (4.6 mmol; 95.8%). Mp=137-138° C. IR ṽ [cm⁻¹]=2974; 1753; 1736; 1663. EI-MS m/z (rel. Int.)=335 (10.61%; M⁺ᐧ). ¹H NMR (300 MHz, CDCl₃) 8.83 (s; 1H; indole-H); 8.12 (dd; J=4.7 Hz; J=9.2 Hz; 1H; indole-H); 8.08 (dd; J=2.7 Hz; J=9.2 Hz; 1H; indole-H); 7.14

(dt; J=2.7 Hz; J=9.2 Hz; 1H; indole-H); 4.44 (q; ³J=7.2 Hz; 2H; OC$\underline{H_2}$CH₃); 1.70 (s; 9H; C(CH₃)₃); 1.45 (t; ³J=7.2 Hz; 3H; OCH₂C$\underline{H_3}$).

The general procedure 2 was then followed using the above product (4.5 mmol, 1.5 g), 3,4,5-trimethoxyphenylacetamide (4.5 mmol, 1.0 g) and 1 M tert.-BuOK (13.5 mmol, 13.5 ml). The purification was achieved by column chromatography (petrolether:ethylacetate:methanol 4.75:4.75:0.5) to yield 3-(5-fluoro-1H-indol-3-yl)-4-(3,4,5-trimethoxyphenyl)-maleinimide (1.7 mmol; 39%) as yellow crystals. Mp=232-233° C. IR $\tilde{v}$ [cm⁻¹]=3289; 1716; 1577. FD-MS m/z (rel. Int.)=398.1 (1.71%; M⁺·). ¹H NMR (300 MHz, DMSO) 11.99 (bs; 1H; indole-NH); 11.07 (bs; 1H; imide-NH); 8.06 (d; ³J=2.6 Hz; 1H; indole-H); 7.44 (dd; J=4.7 Hz; J=8.8 Hz; 1H; indole-H); 6.94 (dt; J=2.3 Hz; J=9.1 Hz; 1H; indole-H); 6.7 (s; 2H; Ar—H); 5.91 (dd; J=2.1 Hz; J=10.7 Hz; 1H; indole-H); 3.67 (s; 3H; OCH₃); 3.43 (s; 6H; 2×OCH₃). Anal. Calcd for C₂₁H₁₇FN₂O₅C, 63.63; H, 4.32; N, 7.07. Found: C, 63.44; H, 4.45; N, 6.86.

Example P 3-(5-Bromo-1H-indol-3-yl)-4-(3,4,5-trimethoxyphenyl)-maleinimide

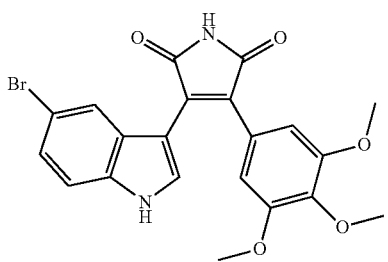 [SMILES: COc1cc(C2=C(c3c[nH]c4ccc(Br)cc34)C(=O)NC2=O)cc(OC)c1OC]

Ethyl 2-(5-brom-1H-indol-3-yl)-2-oxoacetate was prepared using the same procedure as in Example 10. The following amounts were used: 5-bromoindole (6.6 mmol; 1.29 g); ethyloxalylchloride (7.5 mmol; 1.02 g=0.83 ml); pyridine (0.7 ml); diethylether (30 ml). Ethyl 2-(5-bromo-1H-indol-3-yl)-2-oxoacetate (3.5 mmol; 53%) was obtained as pale yellow crystals. Mp=182-183° C. IR $\tilde{v}$ [cm⁻¹]=3224; 1720; 1618. EI-MS m/z (rel. Int.)=297 (100%; M⁺·). ¹H NMR (300 MHz, CDCl₃+DMSO) 11.79 (bs; 1H; NH); 8.09 (d; J=1.1 Hz; 1H; indole-H); 8.01 (d; J=3.3 Hz; 1H; indole-H); 7.01 (m; 2H; indole-H); 4.04 (q; ³J=7.1 Hz; 2H; OC$\underline{H_2}$CH₃); 1.07 (t; ³J=7.1 Hz; 3H; OCH₂C$\underline{H_3}$).

Ethyl-2-[1-(tert.-butoxycarbonyl)-5-bromo-1H-indol-3-yl]-2-oxoacetate was prepared using the same procedure as in Example 10. The following amounts were used: Ethyl 2-(5-bromo-1H-indol-3-yl)-2-oxoacetate (3.5 mmol; 1.05 g); di-tert.-butyldicarbonat (4 mmol; 0.8 g); DMAP; dichloromethan (30 ml). Ethyl-2-[1-(tert.-butoxycarbonyl)-5-bromo-1H-indol-3-yl]-2-oxoacetate was obtained as white crystals (2.6 mmol; 74.3%). Mp=159-160° C. IR $\tilde{v}$ [cm⁻¹]=2962; 1751; 1732; 1663 EI-MS m/z (rel. Int.)=397 (12.17%; M⁺·). ¹H NMR (300 MHz, CDCl₃) 8.78 (s; 1H; indole-H); 8.56 (d; ⁵J=2.0 Hz; 1H; indole-H); 8.05 (d, ³J=8.9 Hz, 1H; indole-H); 7.52 (dd; ⁵J=2.0 Hz; ³J=8.9 Hz; 1H; indole-H); 4.44 (q; ³J=7.1 Hz; 2H; OC$\underline{H_2}$CH₃); 1.70 (s; 9H; C(CH₃)₃); 1.45 (t; ³J=7.1 Hz; 3H; OCH₂C$\underline{H_3}$).

The general procedure 2 was then followed using the above product (2.6 mmol, 1.02 g), 3,4,5-trimethoxyphenylacetamide (2.7 mmol, 0.6 g) and 1 M tert.-BuOK (8 mmol, 8 ml). The purification was achieved by column chromatography (petrolether:ethylacetat:methanol 4.5:4.5:1) to yield 3-(5-bromo-1H-indol-3-yl)-4-(3,4,5-trimethoxyphenyl)-maleinimide (0.68 mmol; 26%) as orange crystals. Mp=259-262° C. IR $\tilde{v}$ [cm⁻¹]=3342; 1708; 1614. FD-MS m/z (rel. Int.)=458.1 (38.24%; M⁺·). ¹H NMR (300 MHz, DMSO) 12.07 (bs; 1H; indole-NH); 11.08 (bs; 1H; imide-NH); 8.05 (d; ³J=2.7 Hz; 1H; indole-H); 7.40 (d; ³J=8.6 Hz; 1H; indole-H); 7.20 (dd; ⁵J=1.6 Hz; ³J=8.6 Hz; 1H; indole-H); 6.68 (s; 2H; Ar—H); 6.38 (s; 1H; indole-H); 3.71 (s; 3H; OCH₃); 3.43 (s; 6H; 2×OCH₃). Anal. Calcd for C₂₁H₁₇BrN₂O₅C, 55.16; H, 3.75; N, 6.13. Found: C, 55.06; H, 3.87; N, 6.01.

Biological Effects of 3-(Indolyl)- and 3-(Azaindolyl)-4-Phenylmaleimide Derivatives The 3-(indolyl)- and 3-(azaindolyl)-4-phenylmaleimide derivatives of the present invention (see Table 1) were investigated for their effect on the viability of vascular endothelial, colon cancer and stomach cancer cell lines, for their antiangiogenic activity as well as for their inhibitory effect on different protein kinases.

Materials & Methods

GSK-3β, VEGFR-2, FLT-3 Kinase Inhibition Assays

The effect of test compounds on the activity of the protein kinases GSK-3β, VEGFR-2 and FLT-3 was evaluated based on half maximal inhibitory concentration (IC₅₀) values determined by Millipore UK Ltd; Gemini Crescent; Dundee Technology Park; Dundee DD2 1SW; UK (IC₅₀Profiler). Detailed protocols can be found at: www.millipore.com/drugdiscovery/dd3/assayprotocols.

Evaluation of Antiangiogenic Activity in a Quantitative Chick Embryo In Vivo Assay The inhibition of angiogenesis (new blood vessel formation) was measured as described in WO2006/061212.

Evaluation of Effect on Viability (MTT Assay)

The antiproliferative activity of test compounds was determined by the 3-(4,5-dimethylthiazol-2-yl)-2,5-diphenyltetrazolium bromide (MTT) assay as described previously (Mosmann, T. et al. (1983) J. Immunol. Methods 65, 55-63). Cells in the exponential growth phase were transferred to 96-well flat-bottom plates. 10,000 viable cells contained in 200 μl cell suspension were plated into each well and incubated over night. Cells were then exposed to various concentrations of test compounds (100 μl/well) for 3 days at 37° C. with 5% CO₂. Subsequently, 10 μl/well MTT stock solution (5 mg/ml; Biomol, Germany) was added and the cells were incubated at 37° C. with 5% CO₂ for 4 hours. 100 μl solubilization solution (10% SDS in 0.01 M HCl) was added and the cells were incubated at 37° C. with 5% CO₂ over night. Plates were read on an ELISA-Reader ELX 800 (BIO-TEK Software KC 4) at 562 nm absorbance. Each experiment was done in triplicate.

Nicoletti Apoptosis Assay by Cell Cycle Analysis

Cancer cells were transferred to 12-well flat-bottomed plates. 1.5×10⁵ viable cells contained in 1 ml cell suspension were plated into each well and incubated over night before exposure with various concentrations of drugs. Subsequently, cells were incubated in 1 ml medium containing various concentrations of test compounds at 37° C. with 5% CO₂. After incubation the cells were washed with PBS, trypsinized, pelleted and mixed with PI buffer (containing 0.1% sodium citrate, 0.1% triton X-100, 50 mg/ml propidium iodide (PI)) and incubated for 1 hour at 4° C. Cell cycle sub-G1 fraction analysis was performed as described previously (Nicoletti, I. et al. (1991) J. Immunol. Methods 139, 271-279) using a flow cytometer (BD FACS Calibur™, BD Biosciences, Heidelberg, Germany). Each experiment was done in triplicate.

The same analysis was performed with HUVEC cells. 1.5× $10^4$ cells were plated into each well and treated with test compounds for 4 days.

Test Compounds (Compounds of Formula (I)) and Cytotoxic Agents

Working solutions of 26 mM test compound in DMSO were prepared and stored in aliquots at −20° C. Irinotecan and topotecan were obtained from the Pharmacy of the University Hospital of Mainz, dissolved in water. Stock solutions of 29.6 mM irinotecan and 4.75 mM topotecan, respectively, were prepared and stored in aliquots at 4° C. The drugs were diluted in culture medium immediately before use to obtain the desired concentrations.

Cell Lines

The human colon cancer cell lines HCT-116, HT-29, Caco-2, SW480 and the stomach cancer cell line MKN-45 were obtained from DSMZ, Germany. HCT-116, HT-29 and SW480 cells were cultured in RPMI1640 supplemented with 10% FCS. MKN-45 in RPMI1640 supplemented with 20% FCS and Caco-2 cells in 80% MEM (with Earle's salts) supplemented with 20% FCS and non-essential amino acids. All cells were maintained at 37° C. and 5% $CO_2$.

Human Umbilical Vein Endothelial Cells (HUVEC) known for mitogenic specifity for VEGF were obtained from the Department of Pathology, University Hospital of Mainz, Germany. The cells were cultured in M199 supplemented with 20% FCS, 1% Pen/Strep, 0.34% GlutaMAX-I, 25 µg/ml Endothelial Cell Growth Supplement (BD Biosciences), 25 µg/ml Heparin sodium (179 USP units/mg; Sigma, Germany) and were maintained at 37° C. and 5% $CO_2$.

Example 1

Compounds of Formula (I) have Different Selectivity Profiles for Protein Kinases VEGFR-2, FLT-3 and GSK-3β

The inhibitory effect of test compounds on protein kinases VEGFR-2, FLT-3 and GSK-3β was investigated using respective kinase inhibition assays and the half maximal inhibitory concentration ($IC_{50}$) values were determined from the assay results (see Table 2). The individual test compounds showed considerable differences in kinase selectivity.

Compounds with azaindole or 1-H indole group, i.e. compounds A, B, C and D, significantly inhibited VEGFR-2 with $IC_{50}$ values in the low nanomolar range. Most potent inhibitors of GSK-3β with $IC_{50}$ values in the low nanomolar range were compounds with N1 hydroxyalkyl or aminoalkyl substituted indole group (compounds F, G, H, and I) as well as compounds with 5- or 6-azaindole group (compounds C and D). FLT-3 was most significantly inhibited by compounds A, B and F. In summary collectives of test compounds with selective kinase profiles were identified, which may allow application specific for a certain tumor or condition while showing less side-effects caused by activity against other kinases.

TABLE 2

Determination of $IC_{50}$ in kinase assays of VEGFR-2, FLT-3 and GSK-3β

| | $IC_{50}$ [nM] | | |
|---|---|---|---|
| Compound | VEGFR-2 | FLT-3 | GSK-3β |
| A | 90 | 166 | 1100 |
| B | 37 | 132 | >10000 |
| C | 48 | 1902 | <10 |

TABLE 2-continued

Determination of $IC_{50}$ in kinase assays of VEGFR-2, FLT-3 and GSK-3β

| | $IC_{50}$ [nM] | | |
|---|---|---|---|
| Compound | VEGFR-2 | FLT-3 | GSK-3β |
| D | 23 | 6268 | 50 |
| E | 373 | 1516 | 215 |
| F | 1885 | 227 | 195 |
| G | 1500 | >1000 | 129 |
| H | 153 | 554 | 3 |
| I | 920 | 556 | 2 |
| J | 1300 | >1000 | 3582 |
| K | >10000 | 1529 | >1000 |
| L | 1209 | 1242 | >1000 |
| M | 9200 | >10000 | 657 |
| N | 2827 | >10000 | 3238 |
| O | 182 | n.d. | n.d. |

Example 2

Compounds of Formula (I) Show Inhibition of Microvessel Formation

The antiangiogenic activity of compounds of the present invention was analyzed using a quantitative chick embryo in vivo assay. After 24 hours incubation, the tested compounds showed up to 82% inhibition of the microvessel formation (Table 3), thus demonstrating significant antiangiogenic activity.

TABLE 3

Inhibition of microvessel formation

| Compound | Drug concentration/pellet | Inhibition of microvessel area |
|---|---|---|
| A | 26 nM | 82% |
| B | 26 nM | 61% |
| C | 26 nM | 32% |
| D | 26 nM | 69% |
| O | 26 nM | 63% |
| P | 26 nM | 35% |

Example 3

Compounds of Formula (I) Induce Apoptosis in HUVEC Cells

Compounds of the present invention were investigated for their effect on the VEGF-dependent proliferation of human umbilical vein endothelial cells (HUVECs) in concentrations in the nanomolar up to low micromolar range. As illustrated in Table 4 a high, dose-dependent pro-apoptotic activity, i.e. significantly increased fraction of sub-G1 cells, was observed in samples incubated with test compounds for 4 days.

TABLE 4

Induction of apoptosis in HUVEC

Sub-G1 Fraction [%]
Compound

| Conc. | A | B | C | D | O | P |
|---|---|---|---|---|---|---|
| 0.79 µM | 25. ± 0.9 | 26.7 ± 1.9 | 48.0 ± 2.3 | 25.7 ± 1.2 | 16.0 ± 1.2 | 24.0 ± 1.9 |
| 2.6 µM | 87.7 ± 2.3 | 49.2 ± 2.2 | 66.3 ± 1.0 | 70.2 ± 2.7 | 73.3 ± 3.2 | 31.6 ± 2.0 |
| 7.9 µM | 88.9 ± 4.0 | 69.5 ± 3.4 | n.d. | 79.9 ± 3.8 | 90.6 ± 5.4 | 54.4 ± 3.2 |

Sub-G1 fraction of untreated cells: 15.4 ± 1.5%

Example 4

Compounds of Formula (I) Reduce the Viability of Human Colon Adenocarcinoma Cells In Vitro The efficacy of test compounds against HT-29 human colon adenocarcinoma cells was measured by MTT assay. All test compounds showed significant dose-dependent cytotoxicity to HT-29 cells when applied in concentrations in the low micromolar range (Table 5).

Significant synergistic effects of test compound A and low dosed irinotecan were shown for Caco-2, SW480, HT-29 and HCT-116 (Table 6). The combination of compound A and topotecan synergistically inhibited apoptosis of Caco-2, MKN-45, SW480 and HT-29 (Table 7). Further test compounds were tested in combination with irinotecan on HT-29 cells (Table 8): All compounds with N1-substituted indole group (compounds F-N) as well as compounds with halogenated indole group (compounds O and P) showed an activity at least comparable with compound A. Some compounds (H,

TABLE 5

Decrease of HT-29 colon cancer cell viability

Viability of HT-29 cells [%] as determined by MTT assay
Compound

| Conc. | A | B | C | D | E | F | G | H |
|---|---|---|---|---|---|---|---|---|
| 2.6 µM | 78.5 ± 3.7 | 64.95 ± 2.16 | 30.38 ± 1.52 | 62.21 ± 0.33 | 114.36 ± 5.2 | 32.29 ± 1.07 | 45.77 ± 3.25 | 68.80 ± 2.48 |
| 7.9 µM | 62.9 ± 1.5 | 45.55 ± 3.71 | 25.80 ± 3.52 | 64.20 ± 0.76 | 98.31 ± 0.9 | 29.32 ± 2.09 | 36.44 ± 1.77 | 70.21 ± 3.72 |
| 26 µM | 53.9 ± 4.8 | 38.50 ± 0.99 | 12.67 ± 2.60 | 39.56 ± 1.90 | 92.64 ± 2.8 | 12.50 ± 0.39 | 17.65 ± 0.13 | 45.73 ± 2.18 |
| 52 µM | 42.8 ± 1.6 | 38.11 ± 5.43 | 4.22 ± 0.44 | 19.21 ± 0.26 | 65.78 ± 1.5 | 8.95 ± 0.65 | 6.68 ± 0.29 | 28.70 ± 0.55 |

Viability of untreated HT-29 cells: 100%

Viability of HT-29 cells [%] as determined by MTT assay
Compound

| Conc. | I | J | K | L | M | N | O | P |
|---|---|---|---|---|---|---|---|---|
| 2.6 µM | 37.85 ± 1.30 | 68.48 ± 8.69 | 39.33 ± 2.60 | 86.50 ± 2.16 | 81.14 ± 2.99 | 66.45 ± 3.10 | 47.83 ± 0.34 | 37.83 ± 0.19 |
| 7.9 µM | 34.70 ± 0.78 | 52.60 ± 0.53 | 38.54 ± 2.43 | 56.92 ± 3.02 | 84.14 ± 2.18 | 49.90 ± 1.32 | 35.55 ± 0.71 | 20.57 ± 0.35 |
| 26 µM | 27.73 ± 1.23 | 32.16 ± 0.90 | 15.81 ± 1.35 | 20.14 ± 1.36 | 53.39 ± 0.10 | 22.58 ± 1.16 | 42.11 ± 0.58 | 7.07 ± 1.37 |
| 52 µM | 25.45 ± 2.26 | 15.00 ± 0.90 | 19.41 ± 1.32 | 24.34 ± 0.98 | 39.33 ± 1.31 | 15.32 ± 1.21 | 17.61 ± 1.81 | 8.68 ± 0.37 |

Viability of untreated HT-29 cells: 100%

Example 5

Combinations of Compounds of Formula (I) and Toposiomerase I Inhibitors Enhance Apoptosis in Human Colon and Gastric Adenocarcinoma Cells and Show Synergistic Effects Test compounds and the topoisomerase I inhibitors irinotecan and topotecan were analyzed for their individual and combined effect in apoptosis assay.

I and L) were even more potent than compound A in combination with irinotecan.

These results demonstrate that the use of compounds of formula (I) in combination with topoisomerase I inhibitors such as irinotecan and topotecan as described in the present application can provide greatly improved effects on gastric and colorectal cancer cells. Thus, increasing the potency of the topoisomerase I inhibitors associated with dose reduction leading to a better tolerance may be achieved and drug resistances of cancer cells may be overcome.

TABLE 6

Enhancement of apoptosis in human colon and gastric adenocarcinoma cell lines by combining compound A and irinotecan

| | Sub-G1 Fraction [%] | | | | |
|---|---|---|---|---|---|
| | Caco-2 | MKN-45 | SW480 | HT-29 | HCT-116 |
| untreated control | 5.70 ± 0.2 | 7.31 ± 0.29 | 4.59 ± 0.03 | 4.70 ± 1.0 | 2.55 ± 1.0 |
| 7.9 µM compound A | 6.00 ± 2.3 | 20.16 ± 1.6 | 9.96 ± 2.3 | 5.90 ± 0.6 | 3.70 ± 2.8 |
| 1.18 µM irinotecan | 18.80 ± 0.8 | 28.97 ± 1.15 | 9.61 ± 0.91 | 17.40 ± 0.98 | 9.86 ± 2.4 |
| 7.9 µM comp. A plus 1.18 µM irinotecan | 43.70 ± 2.2 | 51.44 ± 0.2 | 32.21 ± 0.40 | 57.40 ± 1.6 | 27.90 ± 3.4 |

TABLE 7

Enhancement of apoptosis in human colon and gastric adenocarcinoma cell lines by combining compound A and topotecan

| | Sub-G1 Fraction [%] | | | |
|---|---|---|---|---|
| | Caco-2 | MKN-45 | SW480 | HT-29 |
| Drug-free control | 6.0 ± 2.3 | 7.3 ± 0.3 | 4.6 ± 0.04 | 5.1 ± 1.0 |
| 7.9 µM compound A | 5.9 ± 0.6 | 20.2 ± 1.6 | 10 ± 2.3 | 5.9 ± 0.6 |
| 20 nM topotecan | 31.5 ± 0.08 | 26.15 ± 0.49 | 13.34 ± 0.3 | 7.9 ± 0.8 |
| 7.9 µM compound A plus 20 nM topotecan | 52.07 ± 2.84 | 61.1 ± 1.2 | 38.81 ± 0.88 | 65.6 ± 1.8 |

Example 6

Induction of Apoptosis in HT-29 Cells by Compound a Compared to Vandetanib and Sunitinib Irinotecan combination treatment was analyzed in apoptosis assay using human HT-29 cells. The agents tested in combination with irinotecan included compound A and two comparable receptor tyrosine kinase inhibitors, vandetanib und sinitinib, which are in clinical development for treatment of colorectal cancer.

As illustrated in Table 9, compound A showed a greater induction of apoptosis upon 7 days combination treatment with irinotecan compared with the same treatment regime of vandetanib or sunitinib. This result demonstrates the improved effect of the combination of irinotecan and a compound of formula (I), such as compound A, on colorectal cancer cells in comparison to other receptor tyrosine kinase inhibitors.

TABLE 8

Enhancement of apoptosis in human colon (HT-29) adenocarcinoma cells by combining compounds of formula (I) and irinotecan

| | Sub-G1 Fraction [%] Compound | | | | | | | |
|---|---|---|---|---|---|---|---|---|
| Conc. | A | B | C | D | E | F | G | H |
| 7.9 µM test compound | 4.70 ± 0.50 | 2.32 ± 1.16 | 79.9 ± 4.13 | 21.51 ± 2.89 | 4.22 ± 0.74 | 5.69 ± 0.69 | 4.01 ± 0.66 | 8.08 ± 0.77 |
| 7.9 µM test compound plus 1.18 µM irinotecan | 53.10 ± 3.30 | 22.36 ± 2.80 | 75.69 ± 1.77 | 47.53 ± 0.47 | 25.71 ± 1.97 | 51.00 ± 0.56 | 56.01 ± 0.29 | 71.28 ± 3.51 |

Induction of apoptosis under irinotecan single application 18.3 ± 1.1%
Induction of apoptosis by drug-free control 3.4 ± 0.9%

| | Sub-G1 Fraction [%] Compound | | | | | | | |
|---|---|---|---|---|---|---|---|---|
| Conc. | I | J | K | L | M | N | O | P |
| 7.9 µM test compound | 11.25 ± 0.11 | 2.50 ± 1.73 | 3.17 ± 0.86 | 4.64 ± 0.75 | 10.01 ± 2.16 | 3.01 ± 0.40 | 3.26 ± 2.14 | 1.81 ± 0.36 |
| 7.9 µM test compound plus 1.18 µM irinotecan | 65.71 ± 0.04 | 43.48 ± 1.87 | 50.28 ± 1.31 | 62.32 ± 1.63 | 56.81 ± 3.96 | 49.49 ± 1.82 | 49.69 ± 2.96 | 55.00 ± 0.33 |

Induction of apoptosis under irinotecan single application 18.3 ± 1.1%
Induction of apoptosis by drug-free control 3.4 ± 0.9%

TABLE 9

Comparison of compound A activity with vandetanib and sunitinib in combination treatment with irinotecan

| Compound | Sub-G1 Fraction [%] | | |
|---|---|---|---|
| | 7.9 µM compound A | 10 µM vandetanib | 5 µM sunitinib |
| Single-agent treatment with compound | 8.9 ± 0.8 | 11.1 ± 1.9 | 11.8 ± 1.0 |
| Combination of compound plus 1.18 µM Irinotecan | 49.8 ± 1.30 | 35.2 ± 0.4 | 24.5 ± 1.2 |

Induction of apoptosis under irinotecan single application 17.4 ± 0.6%
Induction of apoptosis by drug-free control 2.9 ± 0.6%

The invention claimed is:

1. A method of treating colorectal or gastric adenocarcinoma in a subject which comprises administering to the subject a therapeutically effective amount of a compound selected from the group consisting of:

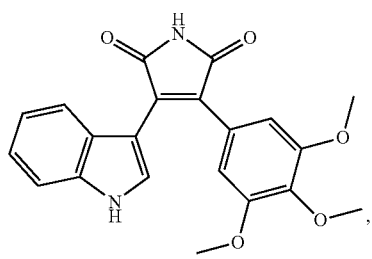

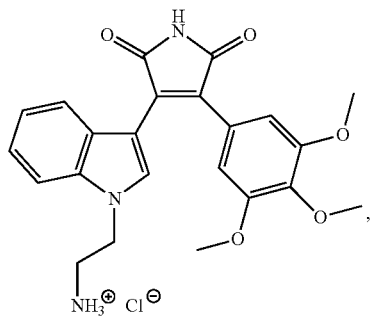

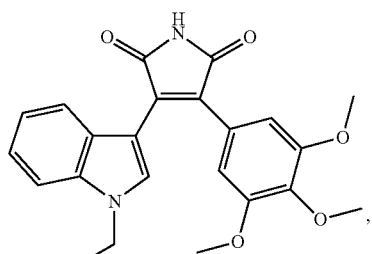

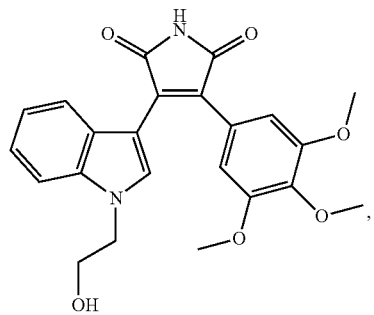

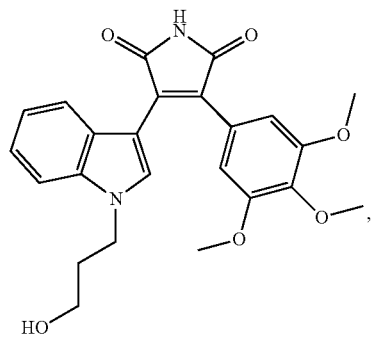

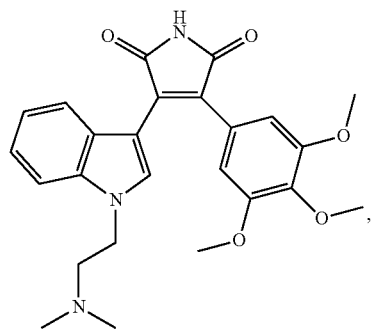

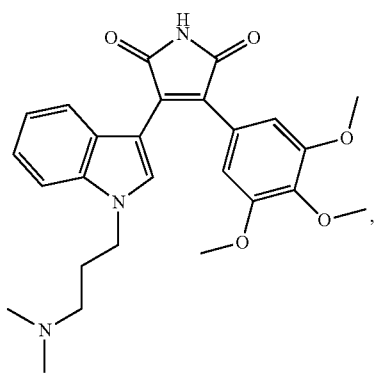

-continued

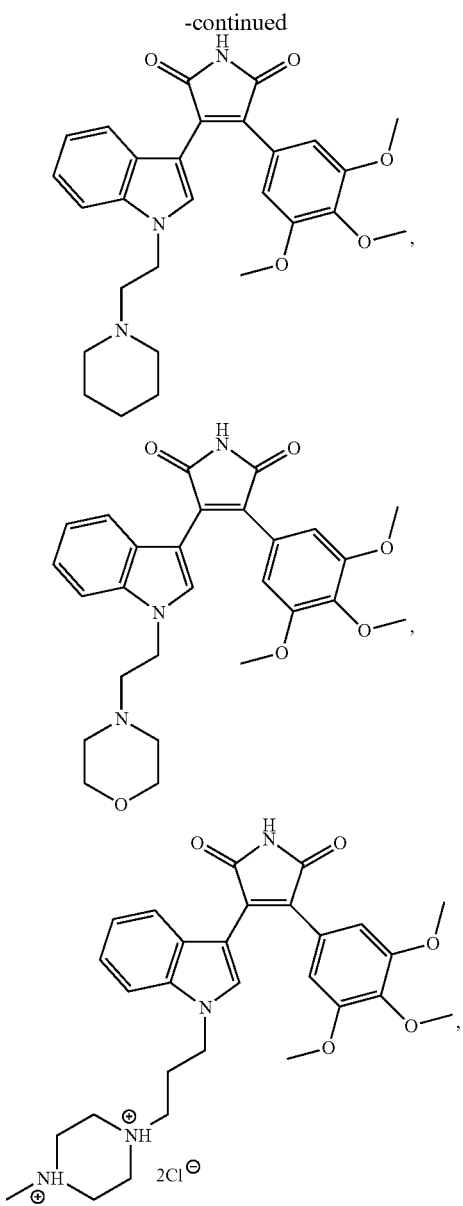

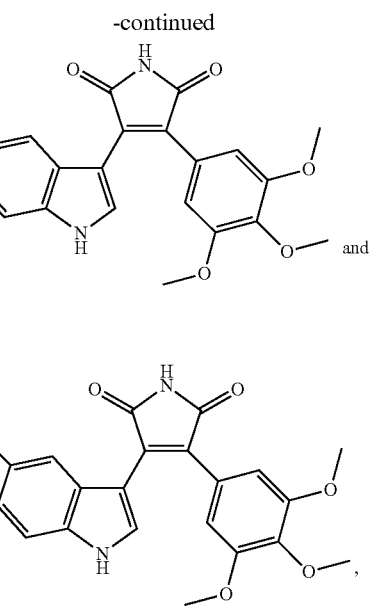

or a physiologically acceptable salt thereof, or a solvate of said compound or of the salt thereof; and further administering to the subject a topoisomerase I inhibitor selected from irinotecan and topotecan.

2. The method of claim 1, wherein the treatment involves promoting readiness of apoptosis or inducing apoptosis of cancer cells.

3. The method of claim 1, wherein the colorectal or gastric adenocarcinoma is a refractory adenocarcinoma.

4. The method of claim 1 for treating colorectal or gastric adenocarcinoma in a subject which consists essentially of administering to the subject a therapeutically effective amount of the compound of claim 1 or a physiologically acceptable salt thereof, or a solvate of the compound of claim 1 or of a salt thereof; and a topoisomerase I inhibitor selected from irinotecan and topotecan.

* * * * *